(12) United States Patent
Wiklof et al.

(10) Patent No.: US 7,448,995 B2
(45) Date of Patent: Nov. 11, 2008

(54) SCANNING ENDOSCOPE

(75) Inventors: Christopher A. Wiklof, Everett, WA (US); Malik I. Amjad, Battle Ground, WA (US); John R. Lewis, Bellevue, WA (US); Frank B. Metting, III, Bothell, WA (US); Christian S. L. Reyerson, Duvall, WA (US); Jianhua Xu, Bothell, WA (US); Clarence T. Tegreene, Bellevue, WA (US)

(73) Assignee: Microvision, Inc., Redmond, WA (US)

( * ) Notice: Subject to any disclaimer, the term of this patent is extended or adjusted under 35 U.S.C. 154(b) by 505 days.

(21) Appl. No.: 10/873,540

(22) Filed: Jun. 21, 2004

(65) Prior Publication Data

US 2005/0020926 A1    Jan. 27, 2005

Related U.S. Application Data

(60) Provisional application No. 60/482,376, filed on Jun. 23, 2003.

(51) Int. Cl.
*A61B 1/00* (2006.01)
*A61B 1/06* (2006.01)
*A61B 6/00* (2006.01)

(52) U.S. Cl. .................. 600/173; 600/160; 600/476

(58) Field of Classification Search ............. 600/129, 600/173, 176, 177, 181, 182, 160, 476, 478, 600/407
See application file for complete search history.

(56) References Cited

U.S. PATENT DOCUMENTS 3,726,281 A   4/1973  Norton et al.
4,589,404 A * 5/1986  Barath et al. ............. 600/108

(Continued)

FOREIGN PATENT DOCUMENTS

DE   2929562    1/1980
DE   2915271    10/1980
DE   10111354   9/2002

OTHER PUBLICATIONS

U.S. Appl. No. 10/880,008, filed Dec. 16, 2004, Seibel et al.

(Continued)

*Primary Examiner*—John P Leubecker
(74) *Attorney, Agent, or Firm*—Kevin D. Wills

(57) ABSTRACT

A scanning endoscope, amenable to both rigid and flexible forms, scans a beam of light across a field-of-view, collects light scattered from the scanned beam, detects the scattered light, and produces an image. The endoscope may comprise one or more bodies housing a controller, light sources, and detectors; and a separable tip housing the scanning mechanism. The light sources may include laser emitters that combine their outputs into a polychromatic beam. Light may be emitted in ultraviolet or infrared wavelengths to produce a hyperspectral image. The detectors may be housed distally or at a proximal location with gathered light being transmitted thereto via optical fibers. A plurality of scanning elements may be combined to produce a stereoscopic image or other imaging modalities. The endoscope may include a lubricant delivery system to ease passage through body cavities and reduce trauma to the patient. The imaging components are especially compact, being comprised in some embodiments of a MEMS scanner and optical fibers, lending themselves to interstitial placement between other tip features such as working channels, irrigation ports, etc.

5 Claims, 17 Drawing Sheets

U.S. PATENT DOCUMENTS

| | | | |
|---|---|---|---|
| 4,973,848 | A | 11/1990 | Kolobanov et al. |
| 5,103,497 | A | 4/1992 | Hicks |
| 5,200,838 | A | 4/1993 | Nudelman et al. |
| 5,269,779 | A | 12/1993 | Sogawa et al. |
| 5,394,237 | A * | 2/1995 | Chang et al. ............... 356/328 |
| 5,742,419 | A | 4/1998 | Dickensheets et al. |
| 5,907,425 | A | 5/1999 | Dickensheets et al. |
| 6,007,208 | A | 12/1999 | Dickensheets et al. |
| 6,013,025 | A | 1/2000 | Bonne et al. |
| 6,057,952 | A | 5/2000 | Kubo et al. |
| 6,088,145 | A | 7/2000 | Dickensheets et al. |
| 6,154,305 | A | 11/2000 | Dickensheets et al. |
| 6,172,789 | B1 | 1/2001 | Kino et al. |
| 6,292,287 | B1 | 9/2001 | Fujinoki |
| 6,294,775 | B1 | 9/2001 | Seibel et al. |
| 6,327,493 | B1 | 12/2001 | Ozawa et al. |
| 6,370,422 | B1 * | 4/2002 | Richards-Kortum et al. 600/478 |
| 6,470,124 | B1 | 10/2002 | Le Gargasson et al. |
| 6,483,626 | B2 | 11/2002 | Suga |
| 6,485,413 | B1 * | 11/2002 | Boppart et al. ............. 600/160 |
| 6,545,260 | B1 | 4/2003 | Katashiro et al. |
| 6,563,105 | B2 * | 5/2003 | Seibel et al. ............ 250/208.1 |
| 6,678,054 | B1 * | 1/2004 | Dress et al. ................. 356/450 |
| 6,749,346 | B1 | 6/2004 | Dickensheets et al. |
| 6,845,190 | B1 | 1/2005 | Smithwick et al. |
| 6,895,270 | B2 * | 5/2005 | Ostrovsky ................... 600/476 |
| 6,950,692 | B2 * | 9/2005 | Gelikonov et al. .......... 600/473 |
| 2001/0055462 | A1 * | 12/2001 | Seibel ........................ 385/147 |
| 2002/0139920 | A1 | 10/2002 | Seibel et al. |
| 2003/0233028 | A1 * | 12/2003 | Tokuda et al. ............... 600/160 |

OTHER PUBLICATIONS

U.S. Appl. No. 10/763,896, filed Aug. 5, 2004, Crossman-Bosworth et al.

U.S. Appl. No. 10/655,482, filed Jun. 24, 2004, Wang et al.

U.S. Appl. No. 09/994,377, filed May 30, 2002, Fauver et al.

U.S. Appl. No. 09/850,594, filed Dec. 27, 2001, Seibel.

Seibel, E.J. et al., Prototype Scanning Fiber Endoscope, *Optical Fibers and Sensors for Medical Applications II, Proceedings of SPIE*, vol. 4616, pp. 173-179, Seattle, Washington (2002).

Seibel, E.J. et al., Microfabricated Optical Fiber with Microlens that Produces Large Field-of-View, Video rate, Optical Beam Scanning for Microendoscopy Applications, *Optical Fibers and Sensors for Medical Applications II, Proceedings of SPIE*, vol. 4957, pp. 46-55, Seattle, Washington (2003).

Seibel, E.J. et al., Unique Features of Optical Scanning, Single Fiber Endoscopy, *Lasers in Surgery and Medicine*, vol. 30, pp. 177-183, Seattle, Washington (2002).

Seibel, E.J. et al., Unique Features of Scanning Fiber Optical Endoscopy, *Annual Fall Meeting Abstracts*, vol. S-40, Seattle, Washington (2000).

Seibel, E.J. et al., Single fiber Flexible Endoscope: General Design for Small Size, High Resolution, and Wide Field of View, *Proceedings of the SPIE, Biomonitoring and Endoscopy Technologies*, 4158, vol 4158, pp. 29-39, Seattle, Washington (2001).

Smithwick, W.Y.J. et al., Control Aspects of the Single Fiber Scanning Endoscope, *Optical Fibers and Sensors for Medical Applications, Proceedings of SPIE*, vol. 4253, pp. 176-188, Seattle, Washington (2001).

Smithwick, W.Y.J et al., Depth Enhancement Using a Scanning Fiber Optical Endoscope, *Optical Biopsy IV, Proceedings of SPIE*, vol. 4613, pp. 222-233, Seattle, Washington (2002).

George M., et al., "A laser-scanning endoscope based on polysilicon micromachined mirrors with enhanced attributes," European Conference on Biomedical Optics (ECBO), Novel Optical Instrumentation for Biomedical Applications, SPIE Proceedings, Jun. 2003.

PCT International Search Report PCT/US2004/019996, Apr. 18, 2005.

* cited by examiner

SCANNING ENDOSCOPE

CROSS REFERENCE TO RELATED APPLICATIONS

This application depends from Provisional Patent Application Ser. No. 60/482,376, entitled SCANNING ENDOSCOPE, filed Jun. 23, 2003, invented by Wiklof, et al., and claims priority therefrom.

FIELD OF THE INVENTION

The present invention relates to scanned beam systems, and more particularly to endoscopes and laparoscopes using scanned beam imaging.

BACKGROUND OF THE INVENTION

Video endoscopes and laparoscopes have been in general use since the 1980s. Laparoscopes are rigid devices that may be used in minimally invasive surgery. Typically, laparoscopes use a proximal, externally mounted hand piece that includes a digital camera. The digital camera collects video images through a series of rod lenses arrayed end-to-end inside a tube that extends into a body cavity of the patient. The camera returns its signal through wires to a console that often includes a display monitor. Also typically mounted on the console is a light source, often based on a xenon lamp. The light source sends light to the hand piece through an optical fiber, where a coupling is made. The light is then sent into the body cavity through optical fibers that run inside the laparoscope tube. Often, the optical fibers terminate at the distal end of the tube in a concentric ring, or partial arc around the periphery of the tube. In use, the illumination power is adjusted to give an image of appropriate brightness on the video monitor.

Endoscopes are typically flexible devices that may be used in diagnostic or other procedures. Modern endoscopes (and some laparoscopes) use a distal tip digital camera that collects light, converts it to an electronic signal, and sends the electronic signal up the flexible tube to a hand piece. The signal is then sent to a console for display similar to the manner of operation of laparoscopes. Illumination is sent to the body cavity in a manner similar to that of laparoscopes, except the illumination fibers typically terminate as a pair of apertures on each side of the camera lens. Endoscopes often include irrigation channels and working channels for instruments, in addition to a steering apparatus that may be used to aim the tip of the endoscope in the direction the clinician wishes to look or push the tube.

Endoscopes and laparoscopes may be end-looking or side-looking. In end-looking devices, the field-of-view is positioned directly in front of the end of the device. Side-looking devices may have their fields-of-view located 70°, or other angle off-axis from the end of the tube. The field-of-view varies according to the application. For instance, colonoscopes (a type of endoscope used to examine the colon) often have a 140° diagonal field-of-view, while laparoscopes may have fields-of-view closer to 70° diagonal.

Instruments may be passed down the working channel of many endoscopes. Forceps and other devices have been developed that may pass within the diameter of the working channel into the body cavity where the clinician uses them to take tissue samples, etc. In the field of laparoscopy, instruments are generally introduced to the procedure through separate small incisions. Often the instruments as well as the laparoscope pass through trocars, or rings that line the incisions to prevent undue binding or damage as well as maintain a seal.

Both laparoscopes and endoscopes may use a pixelated sensor array such as a charge-coupled device (CCD) or complementary metal oxide semiconductor (CMOS) device. In pixelated imagers, each pixel corresponds to an element of an array and each element receives light energy from a conjugate point in the field-of-view for a selected sampling interval. Each element converts light to an electrical signal proportional to the brightness of its conjugate point.

Today's digital endoscopes and laparoscopes may suffer from limited image quality and dynamic range and often exhibit other undesirable artifacts. In the case of distal imaging systems in particular, diameter limitations have been a common hindrance to higher resolution.

OVERVIEW OF THE INVENTION

In its various aspects, the present invention relates to scanned beam imaging systems, and particularly to scanned beam endoscopes, laparoscopes, and other imaging devices that gather an image from a relatively inaccessible location. Many aspects may also be applied to other scanning or scanned beam imaging devices including miniaturized bar code imagers, boroscopes, machine vision cameras, and the like.

Many aspects of the present invention are applicable to rigid and flexible application in both medical and non-medical fields. In many cases, the terms endoscope and laparoscope are used interchangeably and may be understood to refer to a broad range of specific implementations in a range of fields including gastroscopes, enteroscopes, sigmoidoscopes, colonoscopes, laryngoscopes, rhinolaryoscopes, bronchoscopes, duodenoscopes, choledochoscopes, nephroscopes, cystoscopes, hysteroscopes, laparoscopes, arthroscopes, and others.

In one exemplary embodiment according to the present invention, a plurality of colored light sources, for example narrow spectrum sources, combine to form substantially white light. The white light is sent to a distal tip via one or more optical fibers, formed into a beam, and the beam is scanned across a field-of-view (FOV). At least a portion of the light reflected, scattered, refracted, or otherwise perturbed by the FOV is gathered and converted into electrical signals. By combining information about beam position and the amount of light gathered, a digital image may be formed. According to an alternative embodiment, information about beam position may be determined from the image itself.

According to one exemplary embodiment, the colored light sources may be red, green, and blue lasers, light emitting diodes, or other devices. According to other exemplary embodiments, a different number of light sources having differing properties may be combined to form the scanning beam. For example, a pair of red sources differing from each other by several nanometers wavelength may be used to improve discrimination of red objects. In another example, light sources with wavelengths intermediate to red, green, and blue sources may be used to create a system having four, five, six or even more channels with improved color gamut. In yet another example, light sources in the infrared, ultraviolet, or beyond may be combined to form an extended spectrum system.

According to other exemplary embodiments, light sources having therapeutic properties may be used for treatment. For example, high-powered infrared light may be used to cauterize, ultraviolet light may be used to enable phototropic drugs, etc. The combination of narrow wavelength sources may be used to avoid exposure to unwanted wavelengths, for instance when a phototropic drug or photo-diagnostic chemical is generally present but it is desired to activate it only in certain locations. Therapeutic beams may be selectively enabled by the physician or by a remote expert, or alternatively may be automatically enabled based upon image properties. They may be enabled for all of the field of view, for a portion of the field-of-view, or for specific, small spots within the field-of-view.

According to other exemplary embodiments, a plurality of light sources may be combined into a beam that is not color-balanced per se. In such cases, the image may be color-balanced electronically. According to still other exemplary embodiments, it is not necessary to use multiple colored light sources, but rather one or more relatively broadband sources may be used.

According to some embodiments, the light beam is passed concentrically through the center of the scanning mirror, bounced off a first reflector, and returned to the scanning mirror, which scans the beam across the field-of-view. This concentric beam path may be advantageous, for example, for minimizing the size of the imaging tip. Polarization properties of the beam and the first reflector may be manipulated or chosen to maximize signal strength and minimize stray light being admitted to the field-of-view. According to alternative embodiments, polarization is not matched, but rather a semi-transparent mirror returns a portion of the light to the mirror.

Light from the beam may be scattered by, transmitted through, absorbed by, and/or reflected off surfaces in the field-of-view, and may encounter multiple transmission paths through the body cavity. A portion of the light so transmitted is gathered at one or more collection points. The collection point or points may comprise non-imaging collection and detection means, for instance photodiodes distally mounted on the tip. Alternatively, the collection means may comprise optical fibers that collect the light and transmit it to a remote detection unit where the light is converted into electrical signals for further processing. Such gathering fibers may be arranged circumferentially around the scanner module, for example. Alternatively, the light may be de-scanned by the scanning mirror and collected retro-collectively or confocally. In another alternative, collection fibers may be arranged across the tip in interstitial spaces between irrigation channels, working channels, etc. In yet another alternative, separate collection fibers may be inserted into the body cavity, for instance in the form of tools, trocars, or other devices that collect the scattered light remotely from the imaging tip. In another alternative, the tip may be made at least partially translucent to increase the area over which light is gathered.

The endoscope or laparoscope, according to some exemplary embodiments, may use light sources and/or detectors that are mounted in a hand piece. According to alternative exemplary embodiments, the endoscope or laparoscope may include a console that contains light sources and/or detectors. The light may be transmitted to and from optical fibers and the console via a connector that may also include electrical connections for powering and monitoring the scanner, for providing display information to the hand piece, for controlling operation of the system, etc.

According to exemplary embodiments, the scanner may be a MEMS scanner that operates in a progressive scan pattern or a bi-sinusoidal scan pattern, for example. In some embodiments, the scanner is operated by magnetic drive. In alternative embodiments the scanner is operated by electrostatic drive, by a combination of magnetic and electrostatic drive, or other known means such as piezoelectric or bi-morph drive.

The MEMS scanner may be a bulk micro-machined MEMS scanner, a surface micro-machined device, or other type as is known to the art. The surface of the mirror may be flat or alternatively include optical power to help shape the beam.

According to some exemplary embodiments, the field-of-view may be controlled by the amplitude of the drive signal, a lower amplitude signal creating somewhat less angular motion and hence a smaller field-of-view, and a higher amplitude signal creating greater angular motion and hence a larger field-of-view.

According to an exemplary embodiment, a beam collimating or focusing device such as one or more of a lens, mirror, aperture, and polished fiber end may be used to shape the beam. One or more collimating devices may change position or shape to control the shape of the beam. The shape of the beam may be changed in concert with field-of-view to maintain a relatively constant fill factor of the spot size with respect to spot spacing. Alternatively or additionally, the beam shape may be controlled by the user or by automated means to maintain optimal focus.

According to an exemplary embodiment, the working channel may be automated, based, for example, upon image analysis. The outer covering or sheath of the tip may include lubrication and/or medication ports to help reduce the need for other medication and to reduce patient discomfort, morbidity, and/or mortality.

According to an exemplary embodiment, the light gathering means may be cross-polarized to the beam to reduce or eliminate specular reflections.

According to an exemplary embodiment, the device may include monitoring means such as hemoglobin oxygenation monitoring or carbon dioxide monitoring. Doppler measurement may be used to determine blood flow.

According to another exemplary embodiment, the FOV may be illuminated with a variable-intensity source. The variable intensity source may be formed, for instance, by scanning one or more beams of light across at least portions of the field-of-view while modulating the intensity of the beam or beams. In this way, darker and/or more distant regions may be illuminated more while lighter and/or closer regions are illuminated less.

According to another exemplary embodiment, the color balance of a field-of-view or portions of a field-of-view may be modified by differentially illuminating the scene with illuminators of differing color. It is possible to drive the illuminator in such a way that a portion up to substantially all scene information is exhibited as the inverse of the data used to drive the variable illumination. At one limit, the field-of-view may be differentially illuminated to produce substantially uniform light scatter at a detector. In this case, image information may be retrieved wholly or substantially by a frame buffer used to drive the differential illuminator. This mode may be especially advantageous for non-imaging detectors such as PIN photodiodes, avalanche photodiodes, photomultiplier tubes, and the like.

According to other exemplary embodiments, a scanned beam illuminator may be combined with an imaging detector such as a pixelated imager. Variable illumination may be applied to effectively extend the dynamic range of the system, allowing for faster, smaller, or otherwise modified sensors. Variable illumination may similarly be used to extend the depth-of-field of the apparatus by applying additional illuminating energy to more distant or darker regions.

According to another exemplary embodiment, the field-of-view may be "probed" for image data. In this case, especially bright illumination may be switched on for an instant to determine the optical characteristics of one or a few dark or distant spots, and then switched off for a time sufficient to meet safety or other requirements. During subsequent frames, other spots may be similarly probed.

DETAILED DESCRIPTION OF THE INVENTION

Figure 1:
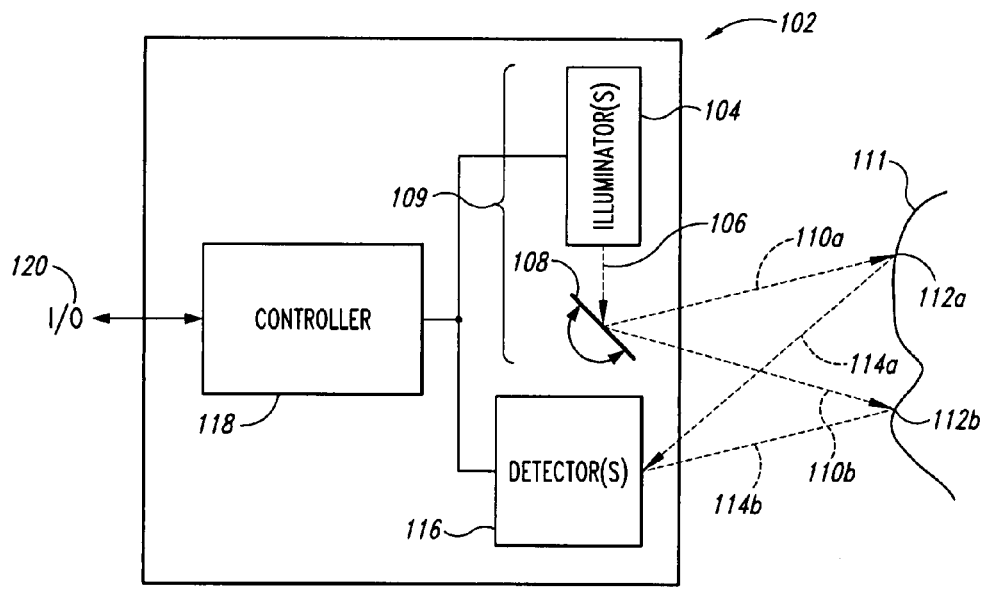
FIG. 1 is a block diagram of a simple scanned beam imager.

FIG. 1 shows a block diagram of a scanned beam imager 102. An illuminator 104 creates a first beam of light 106. A scanner 108 deflects the first beam of light across a field-of-view (FOV) to produce a second scanned beam of light 110, shown in two positions 110a and 110b. The scanned beam of light 110 sequentially illuminates spots 112 in the FOV, shown as positions 112a and 112b, corresponding to beam positions 110a and 110b, respectively. While the beam 110 illuminates the spots 112, the illuminating light beam 110 is reflected, absorbed, scattered, refracted, or otherwise affected by the properties of the object or material to produced scattered light energy. A portion of the scattered light energy 114, shown emanating from spot positions 112a and 112b as scattered energy rays 114a and 114b, respectively, travels to one or more detectors 116 that receive the light and produce electrical signals corresponding to the amount of light energy received. The electrical signals drive a controller 118 that builds up a digital image and transmits it for further processing, decoding, archiving, printing, display, or other treatment or use via interface 120.

Light source 104 may include multiple emitters such as, for instance, light emitting diodes (LEDs), lasers, thermal sources, arc sources, fluorescent sources, gas discharge sources, or other types of illuminators. In some embodiments, illuminator 104 comprises a red laser diode having a wavelength of approximately 635 to 670 nanometers (nm). In another embodiment, illuminator 104 comprises three lasers; a red diode laser, a green diode-pumped solid state (DPSS) laser, and a blue DPSS laser at approximately 635 nm, 532 nm, and 473 nm, respectively. While laser diodes may be directly modulated, DPSS lasers generally require external modulation such as an acousto-optic modulator (AOM) for instance. In the case where an external modulator is used, it is considered part of light source 104. Light source 104 may include, in the case of multiple emitters, beam combining optics to combine some or all of the emitters into a single beam. Light source 104 may also include beam-shaping optics such as one or more collimating lenses and/or apertures. Additionally, while the wavelengths described in the previous embodiments have been in the optically visible range, other wavelengths may be within the scope of the invention.

Light beam 106, while illustrated as a single beam, may comprise a plurality of beams converging on a single scanner 108 or onto separate scanners 108.

Some embodiments use a MEMS scanner. A MEMS scanner may be of a type described in, for example; U.S. Pat. No. 6,140,979, entitled SCANNED DISPLAY WITH PINCH, TIMING, AND DISTORTION CORRECTION and commonly assigned herewith; U.S. Pat. No. 6,245,590, entitled FREQUENCY TUNABLE RESONANT SCANNER AND METHOD OF MAKING and commonly assigned herewith; U.S. Pat. No. 6,285,489, entitled FREQUENCY TUNABLE RESONANT SCANNER WITH AUXILIARY ARMS and commonly assigned herewith; U.S. Pat. No. 6,331,909, entitled FREQUENCY TUNABLE RESONANT SCANNER and commonly assigned herewith; U.S. Pat. No. 6,362,912, entitled SCANNED IMAGING APPARATUS WITH SWITCHED FEEDS and commonly assigned herewith; U.S. Pat. No. 6,384,406, entitled ACTIVE TUNING OF A TORSIONAL RESONANT STRUCTURE and commonly assigned herewith; U.S. Pat. No. 6,433,907, entitled SCANNED DISPLAY WITH PLURALITY OF SCANNING ASSEMBLIES and commonly assigned herewith; U.S. Pat. No. 6,512,622, entitled ACTIVE TUNING OF A TORSIONAL RESONANT STRUCTURE and commonly assigned herewith; U.S. Pat. No. 6,515,278, entitled FREQUENCY TUNABLE RESONANT SCANNER AND METHOD OF MAKING and commonly assigned herewith; U.S. Pat. No. 6,515,781, entitled SCANNED IMAGING APPARATUS WITH SWITCHED FEEDS and commonly assigned herewith; and/or U.S. Pat. No. 6,525,310, entitled FREQUENCY TUNABLE RESONANT SCANNER and commonly assigned herewith; all hereby incorporated by reference.

A 2D MEMS scanner 108 scans one or more light beams at high speed in a pattern that covers an entire 2D FOV or a selected region of a 2D FOV within a frame period. A typical frame rate may be 60 Hz, for example. Often, it is advantageous to run one or both scan axes resonantly. In one embodiment, one axis is run resonantly at about 19 KHz while the other axis is run non-resonantly in a sawtooth pattern so as to create a progressive scan pattern. A progressively scanned bi-directional approach with a single beam scanning horizontally at scan frequency of approximately 19 KHz and scanning vertically in sawtooth pattern at 60 Hz can approximate an SVGA resolution. In one such system, the horizontal scan motion is driven electrostatically and the vertical scan motion is driven magnetically. Alternatively, both the horizontal and vertical scan may be driven magnetically or capacitively. Electrostatic driving may include electrostatic plates, comb drives or similar approaches. In various embodiments, both axes may be driven sinusoidally or resonantly.

Several types of detectors may be appropriate, depending upon the application or configuration. For example, in one embodiment, the detector may include a simple PIN photodiode connected to an amplifier and digitizer. In this configuration, beam position information may be retrieved from the scanner or, alternatively, from optical mechanisms, and image resolution is determined by the size and shape of scanning spot 112. In the case of multi-color imaging, the detector 116 may comprise more sophisticated splitting and filtering to separate the scattered light into its component parts prior to detection. As alternatives to PIN photodiodes, avalanche photodiodes (APDs) or photomultiplier tubes (PMTs) may be preferred for certain applications, particularly low light applications.

In various approaches, simple photodetectors such as PIN photodiodes, APDs, and PMTs may be arranged to stare at the entire FOV, stare at a portion of the FOV, collect light retro-collectively, or collect light confocally, depending upon the application. In some embodiments, the photodetector 116 collects light through filters to eliminate much of the ambient light.

The present device may be embodied as monochrome, as full-color, and even as a hyper-spectral. In some embodiments, it may also be desirable to add color channels between the conventional RGB channels used for many color cameras. Herein, the term grayscale and related discussion shall be understood to refer to each of these embodiments as well as other methods or applications within the scope of the invention. In the control apparatus and methods described below, pixel gray levels may comprise a single value in the case of a monochrome system, or may comprise an RGB triad or greater in the case of color or hyperspectral systems. Control may be applied individually to the output power of particular channels (for instance red, green, and blue channels), may be applied universally to all channels, or may be applied to a subset of the channels.

In some embodiments, the illuminator may emit a polarized beam of light or a separate polarizer (not shown) may be used to polarize the beam. In such cases, the detector 116 may include a polarizer cross-polarized to the scanning beam 110. Such an arrangement may help to improve image quality by reducing the impact of specular reflections on the image.

Figure 2:
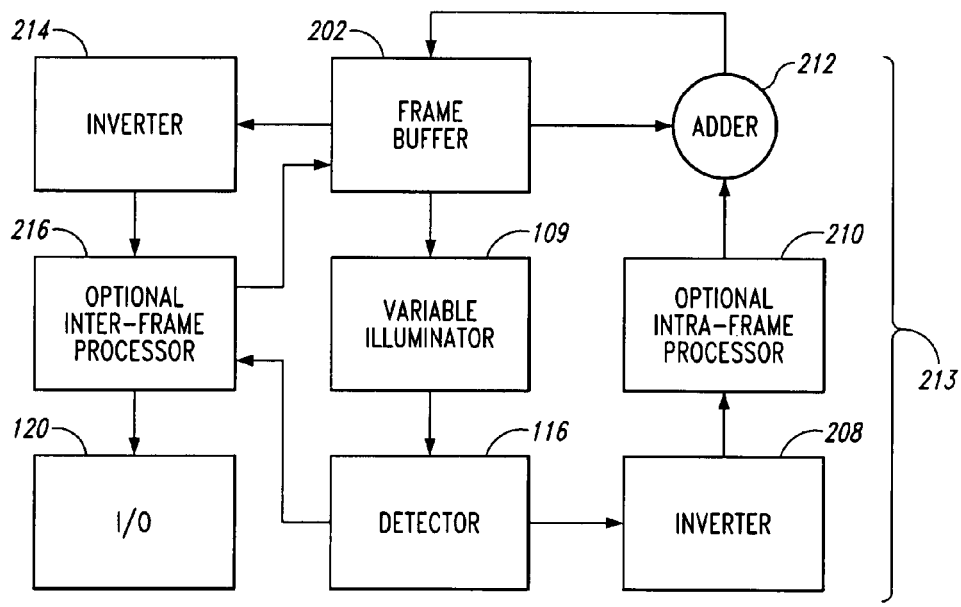
FIG. 2 is a block diagram of an apparatus and method for modifying illuminator power.

FIG. 2 is a block diagram that illustrates one control schema for adjusting illumination intensity. Initially, a drive circuit drives the light source based upon a pattern which may be embodied as digital data values in a frame buffer 202. The frame buffer 202 drives variable illuminator 109, which may, for instance comprise an illuminator and scanner as in FIG. 1. For each spot or region, the amount of scattered light is detected and converted into an electrical signal by detector 116. Detector 116 may include an A/D converter that outputs the electrical signal as a binary value, for instance. One may refer to this detected value as a residual. The residual is inverted by inverter 208, and is optionally processed by optional intra-frame image processor 210. The inverted residual or processed value is then added to the corresponding value in the frame buffer 202 by adder 212. This proceeds through the entire frame or FOV until all spots have been scanned and their corresponding frame buffer values modified. The process is then repeated for a second frame, a third frame, etc. until all spot residuals have converged. In some embodiments and particularly that represented by FIG. 4*a*, the pattern in the frame buffer represents the inverse of the real-world image in the FOV at this point, akin to the way a photographic negative represents the inverse of its corresponding real-world image.

Inverter 208, optional intra frame processor 210, and adder 212 comprise leveling circuit 213.

The pattern in the frame buffer 202 is read out and inverted, by inverter 214. The inverted pattern may be subjected to optional inter-frame image processing by optional inter-frame image processor 216 and then output to a display, to storage, to additional processing, etc. by input/output 120.

Optional intra-frame image processor 210 includes line and frame-based processing functions to manipulate and override imager control. For instance, processor 210 can set feedback gain and offset to adapt numerically dissimilar illuminator controls and detector outputs, can set gain to eliminate or limit diverging tendencies of the system, and can also act to accelerate convergence and extend system sensitivity. These latter aspects will be discussed in more detail elsewhere. To ease understanding, it will be assumed herein that detector and illuminator control values are numerically similar, that is one level of detector grayscale difference is equal to one level of illuminator output difference.

As a result of the convergence of the apparatus of FIG. 2, spots that scatter a small amount of signal back to the detector become illuminated by a relatively high beam power while spots that scatter a large amount of signal back to the detector become illuminated with relatively low beam power. Upon convergence, the overall light energy received from each spot may be substantially equal.

One cause of differences in apparent brightness is the light absorbance properties of the material being illuminated. Another cause of such differences is variation in distance from the detector. Because of the inherently adaptive nature of the illumination in the present system, greater depth-of-field often results as a natural byproduct. Furthermore, such increased depth-of-field may be realized with systems having lower illuminator output power and lower power consumption than would be possible otherwise. Because a substantially or approximately correct amount of optical power is output to any one spot, spots are not substantially over-illuminated. Compared to other systems that must illuminate all spots sufficiently to capture determinate energy from the darkest spots of interest in the FOV, the present system may output that relatively high amount of illumination energy only to those specific darkest spots of interest, other spots with higher apparent brightness receiving lower illumination energy. Furthermore, illumination output energy is frequently limited by comfort and/or safety requirements. Because such safety regulations typically rely on measurements of incident energy integrated over a relatively large spot corresponding to the pupil size of the human eye and over a relatively long period of time, a system that limits illumination energy both spatially and temporally stands to have an advantage in achieving a numerically lower, nominally safer classification. Therefore, in some applications, the system may achieve high scan range at a restrictive safety classification.

Optional intra-frame image processor 210 and/or optional inter-frame image processor 216 may cooperate to ensure compliance with a desired safety classification or other brightness limits. This may be implemented for instance by system logic or hardware that limits the total energy value for any localized group of spots corresponding to a range of pixel illumination values in the frame buffer. Further logic may enable greater illumination power of previously power-limited pixels during subsequent frames. In fact, the system may selectively enable certain pixels to illuminate with greater power (for a limited period of time) than would otherwise be allowable given the safety classification of a device. In this way, the system can probe distant and/or dark regions of the FOV over multiple frames, acquiring grayscale values for such spots without exceeding desired power limits.

Figure 3:
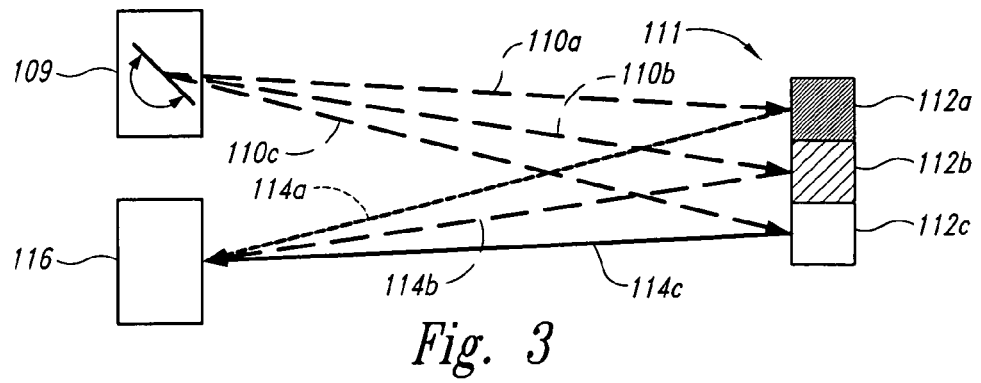
FIG. 3 is a conceptual diagram showing an embodiment for illuminating a FOV and an initial state for an illuminator that is dynamically adjusted. The illumination energy is held constant and the amount of scattered energy received at the detector varies proportionally to the apparent brightness of the spot.
Figure 4A:
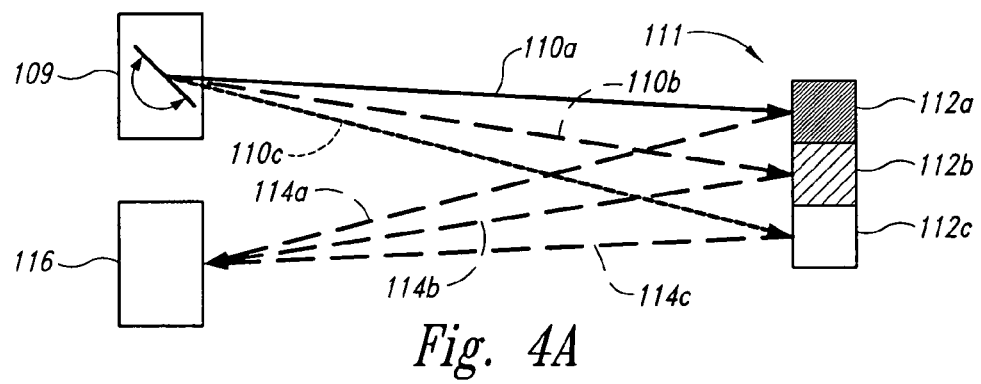
FIG. 4a is a conceptual diagram showing a converged state for an illuminator that has been programmed to provide a flat-field or leveled scatter. The illumination energy is modified in a manner inversely proportional to the apparent brightness of each spot to result in substantially the same amount of received energy at the detector.
Figure 4B:
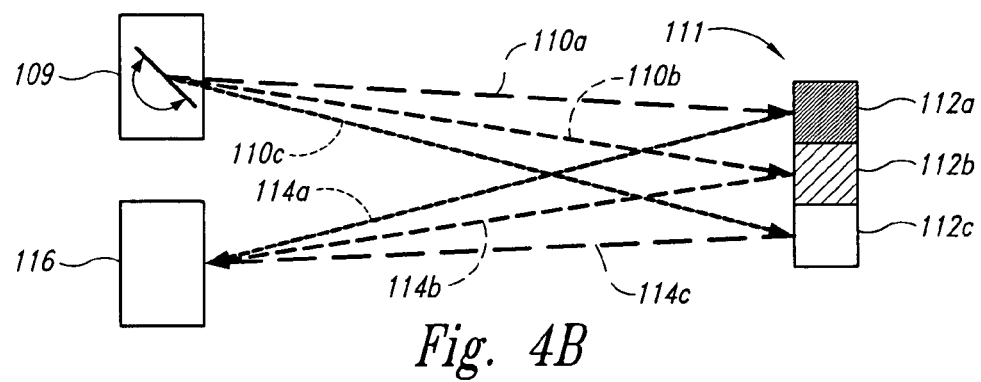
FIG. 4b is a conceptual diagram showing a converged state for an illuminator that has been programmed to compress FOV dynamic range somewhat but still maintain differences in apparent brightness.

The effect of the apparatus of FIG. 2 may be more effectively visualized by referring to FIGS. 3, 4a, and 4b. FIG. 3 illustrates a state corresponding to an exemplary initial state of frame buffer 202. A beam of light 110 produced by a variable illuminator 109 is shown in three positions 110a, 110b, and 110c, each illuminating three corresponding spots 112a, 112b, and 112c, respectively. Spot 112a is shown having a relatively low apparent brightness, spot 112b has a medium apparent brightness, and spot 112c has a relatively high apparent brightness, as indicated by the dark gray, medium gray and light gray shading, respectively.

In an initial state corresponding to FIG. 3, the illuminating beam 110 may be powered at a medium energy at all locations, illustrated by the medium dashed lines impinging upon spots 112a, 112b, and 112c. In this case, dark spot 112a, medium spot 112b, and light spot 112c return low scattered signal 114a, medium scattered signal 114b, and high scattered signal 114c, respectively to detector 116. Low scattered signal 114a is indicated by the small dashed line, medium scattered signal 114b is indicated by the medium dashed line, and high scattered signal 114c is indicated by the solid line.

FIG. 4a illustrates a case where the frame buffer 202 has been converged to a flat-field response. After such convergence, light beam 110 produced by variable illuminator 109 is powered at level inverse to the apparent brightness of each spot 112 it impinges upon. In particular, dark spot 112a is illuminated with a relatively powerful illuminating beam 110a, resulting in medium strength scattered signal 114a being returned to detector 116. Medium spot 112b is illuminated with medium power illuminating beam 110b, resulting in medium strength scattered signal 114b being returned to detector 116. Light spot 112c is illuminated with relatively low power illuminating beam 110c, resulting in medium strength scattered signal 114c being returned to detector 116. In the case of FIG. 4a, image information is no longer completely determined by the strength of the signals being returned to the detector, but rather by the power of the beams used to illuminate the FOV.

Of course it is possible and in some cases may be preferable not to illuminate the FOV such that all spots return substantially the same energy to the detector. For example, it may be preferable to compress the returned signals somewhat to preserve the relative strengths of the scattered signals, but move them up or down as needed to fall within the dynamic range of detector 116. FIG. 4b illustrates this variant of operation. In this case, illumination beams 110 are modulated in their intensity by variable illuminator 109. Beam 110a is increased in power somewhat in order to raise the power of scattered signal 114a to fall above the detection floor of detector 116 but still result in scattered signal 114a remaining below the strength of other signals 114b scattered by spots 112b having higher apparent brightness. The detection floor may correspond for example to quantum efficiency limits, photon shot noise limits, electrical noise limits, or other limits. Conversely, apparently bright spot 112c is illuminated with beam 110c, decreased in power somewhat in order to lower the power of scattered signal 114c to fall below the detection ceiling of detector 116, but still remain higher in strength than other scattered signals 114b returned from other spots 112b with lower apparent brightness. The detection ceiling of detector 116 may be related for instance to full well capacity for integrating detectors such as CCD or CMOS arrays, non-linear portions of A/D converters associated with non-pixelated detectors such as PIN diodes, or other actual or arbitrary limits set by the designer. Of course, illuminating beam powers corresponding to other spots having scattered signals that do fall within detector limits may be similarly modified in linear or non-linear manners depending upon the requirements of the application. For instance, in applications where grayscale information is desirable, a group of spots having successively increasing apparent brightness may be illuminated by beams having successively decreasing energy, resulting in a spread of reflectance values across the dynamic range of the detector. Conversely, in applications where it is desirable to maximize gamma and maximize contrast, it may be desirable to choose illumination energy based on a global or local threshold algorithm that tends to force scattered signal strengths one way or the other toward the low or high limits of the detector.

Figure 5:
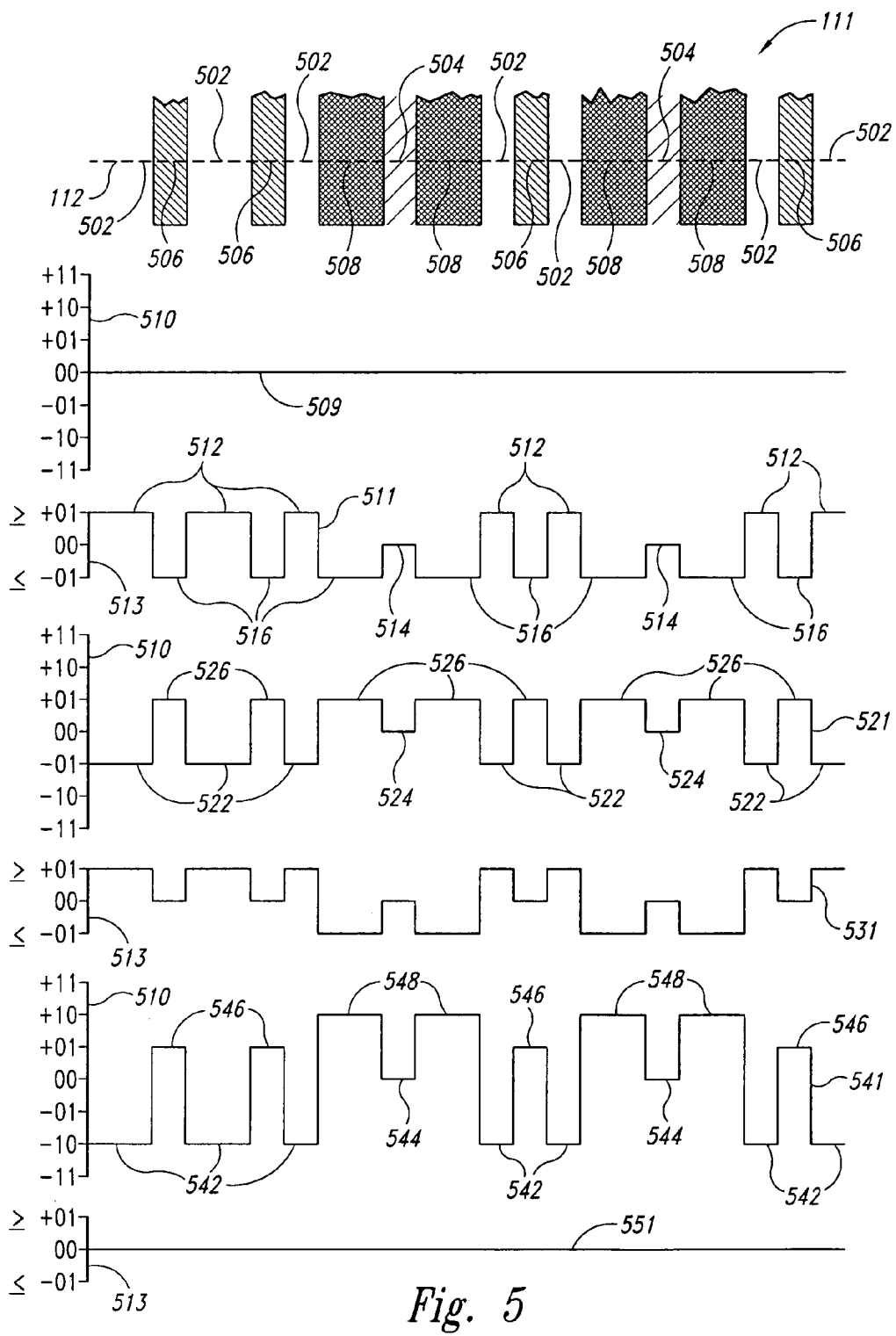
FIG. 5 is a diagram showing idealized waveforms for converging illuminator power per the method of FIG. 4a over several frames for an exemplary 1D FOV.

FIG. 5 is an example of how reflectance values for several spots along a linear scan path might be converged to a substantially constant reflectance value with grayscale values being retained as the inverse of the illumination beam power profile for the scan path. A FOV 111 comprises a scan path 112 having a plurality of spots that may be categorized by reflectance value or apparent brightness level. The reflectance categories include white spots 502, light gray spots 504, medium gray spots 506 and black spots 508. Shown below FOV 111 are several vertically aligned waveforms. Waveform 510 illustrates the illuminator power corresponding to scan path 112. In this example, the illuminator power is held constant for the first scan at a level of 00 out of a possible 7 binary values ranging from −11 to +11.

Waveform 511 is an idealized response from a detector having dynamic range limited to three states: 00 (nominal), $\geq +01$, and $\geq -01$. It ignores optical effects such as Gaussian distortion and assumes gain equivalent to illuminator gain—i.e. ±01 detector units correspond to ±01 illuminator units. In waveform 511, a 00 strength beam swamps the detector when scattered from white spots 502. This is seen by detector values 512 at the high rail ($\geq$+01) in locations corresponding to white spots 502. Conversely, a 00 strength beam reflected from medium gray spots 506 and from black spots 508 results in an undetectable response of $\leq$−01 in waveform locations 516 corresponding to spots 506 and 508. Light gray spots 504 scatter a medium energy signal corresponding to 00 detector response levels 514.

In accordance with the process of FIG. 2, detector waveform 511 is inverted and added to illuminator waveform 509 to produce new illuminator waveform 521. Because initial illuminator waveform 509 was constant, illuminator waveform 521 is simply the inverse of detector waveform 511, with low −01 power regions 522 corresponding to high detected energy regions 512, medium 00 power regions 524 corresponding to medium detected energy regions 514, and high +01 power regions 526 corresponding to low detected energy regions 516.

Beam 112 is then scanned across FOV 111 again using illuminator power waveform 521 which may, for instance, be implemented in the form of a frame buffer. Detector waveform 531 results from the second pass of beam 112. This time, medium gray spots 506 have joined light gray spots 504 in falling within the dynamic range of the detector, but there are still spots that fall outside the range of the detector. Detector waveform 531 is inverted and added to previous illuminator waveform 521 to produce third pass illuminator waveform 541 comprising power levels 542 of −10 corresponding to white spots 112, levels 544 of 00 corresponding to light gray spots 504, levels 546 of +01 corresponding to medium gray spots 506, and levels 548 of +11 corresponding to black spots 508. Beam 112 is finally scanned across FOV 111 using illuminator power waveform 541. Resulting detector power waveform 551 is constant and within the dynamic range 513 of the detector, indicating complete convergence. Thus the inverse of illuminator power waveform 541 has become an image of linear scan path 112 across FOV 111. Consequently, by comparing spots against scale 510, we can see that white spots 502 have a grayscale value of +10, light gray spots 504 have a grayscale value of 00, medium gray spots 506 have a grayscale value of −01, and black spots 508 have a grayscale value of −10.

As can be seen, the system can record an image having a dynamic range greater than that of the detector. In the example of FIG. 5, the image was determined to have a grayscale range of 5 levels (−10 to +10) whereas the detector had only one determinate grayscale level.

Figure 6:
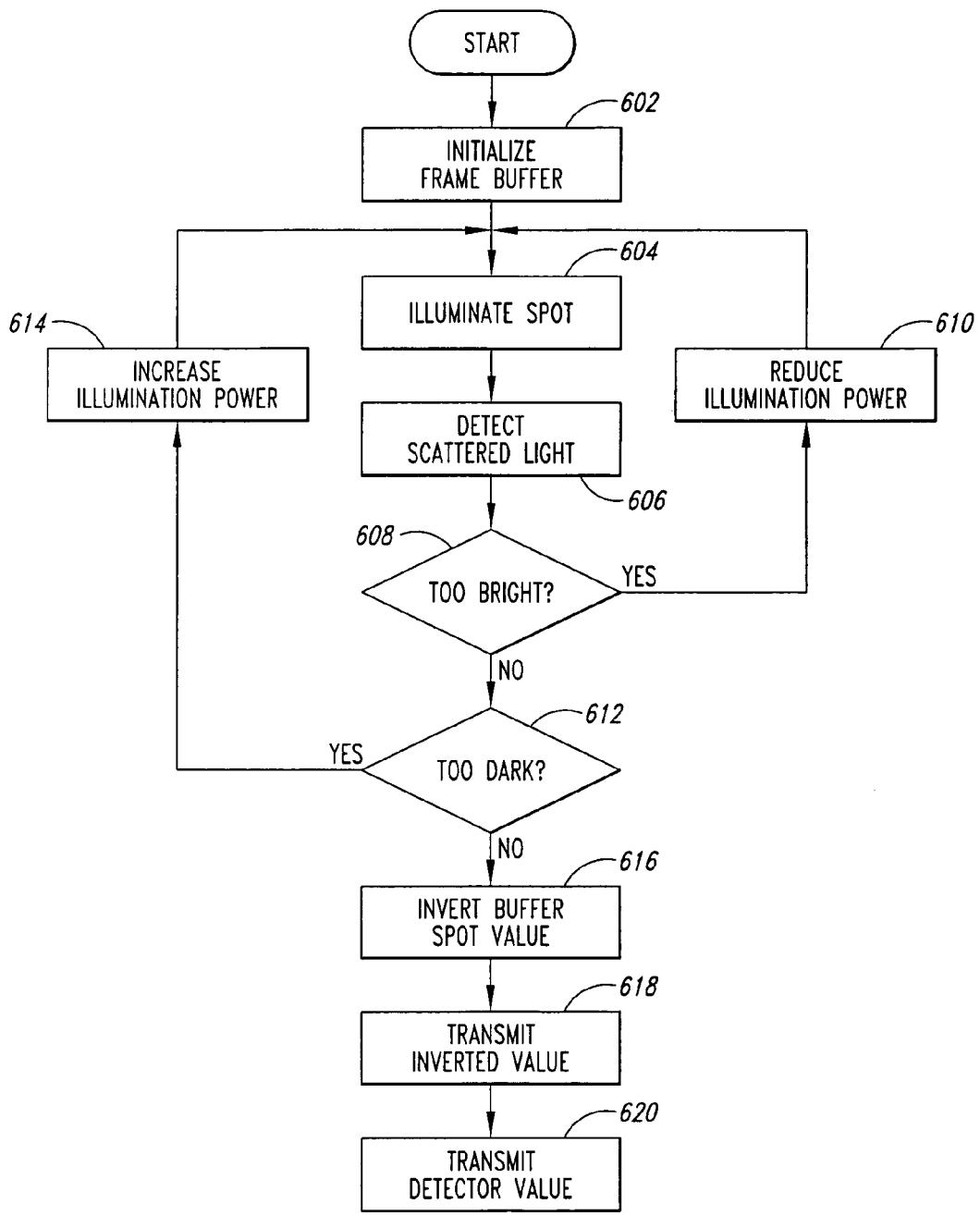
FIG. 6 is a flow chart showing how a pixel value may be converged.

FIG. 6 is a flowchart that shows logic for an embodiment of illuminator power adjustment. In step 602, the frame buffer is initialized. In some embodiments, it may be set to a fixed initial value near the middle, lower end, or upper end of its range. Alternatively, it may be set to a quasi-random pattern designed to test a range of values. In yet other embodiments, its value may be informed by previous pixels in the current frame, some approaches being described in FIGS. 8 and 9. In still other embodiments, its value may be informed by previous frames or previous images.

Using the initial frame buffer value, a spot is illuminated and its scattered light detected as per steps 604 and 606, respectively. If the detected signal is too strong per decision step 608, illumination power is reduced per step 610 and the process repeated starting with steps 604 and 606. If the detected signal is not too strong, it is tested to see if it is too low per step 612. If it is too low, illuminator power is adjusted upward per step 614 and the process repeated starting with steps 604 and 606.

Thresholds for steps 608 and 612 may be set in many ways. For detectors that are integrating, such as a CCD detector for instance, the lower threshold may be set at noise equivalent power (NEP) (corresponding to photon shot noise or electronic shot noise, for example) and the upper threshold set at full well capacity. Instantaneous detectors such as photodiodes typically are limited by non-linear response at the upper end of their range and limited by NEP at the lower end of their range. Accordingly, upper and lower thresholds may be set by these limits in order to maximize grayscale resolution. Alternatively, upper and lower thresholds may be programmable depending upon image attributes, application, user preferences, illumination power range, electrical power saving mode, etc.

Additionally, upper and lower thresholds used by steps 608 and 612 may be variable across the FOV. For instance, when the apparatus is used as a dynamic range compressor as illustrated by FIG. 4b, illuminator energy for a given spot may be selected according to the range of illumination energies and/or detected scatter from the range of relevant spots across the FOV. For instance, whereas a medium gray spot 112b may require only a little illumination power to raise its scatter or reflectance up above the minimum level required for detection in the absence of additional, darker spots; the presence of additional darker spots 112a may dictate a somewhat higher step 612 minimum threshold for that spot in order to raise its apparent brightness high enough in the detector dynamic range to make room for additional, darker spots to also fall within that dynamic range.

After a scattered signal has been received that falls into the allowable detector range, the detector value may be inverted per optional step 616 and transmitted for further processing, storage, or display in optional step 618. Steps 616 and 618 are identified as generally optional depending upon the application.

For applications involving scanned beam imaging and when the illuminator power itself contains a significant portion of pixel information, it may be necessary to invert and transmit pixel illuminator power. On the other hand, when the range between upper and lower thresholds is large (for steps 608 and 612, respectively), illuminator power may be used essentially to compensate for relatively large-scale differences across the FOV with most pixel information being retained in the detector value. This may be used, for instance, when illuminator power modulation is used to compensate for overall FOV reflectivity, range, transmissivity, or other effect that modifies the signal in a gross sense. For some applications, most or all of the useful image information may then be determined by the detector and illuminator power omitted from further processing.

In addition to or, as illustrated above, instead of transmitting illuminator power for further operations, the detector value may be transmitted as in optional step 620. In some applications and particularly those where the detector dynamic range is very limited, there may be very little effective image information in the detector value resulting from the selected illuminator power, and transmission of the detector value may be omitted.

In still other applications significant useful portions of the image data may be present in both the illuminator power and the detector value. An example of this type of application is where illuminator power is used to extend the working range of the device and most of the image information is present in the detector value, but the few bits of apparent pixel brightness information retained by illuminator power act as the most significant bits of the pixel value.

Feedback or feed-forward control schemas for the methodology described above may be implemented, for example, as algorithmic adjustments or as table look-ups as determined according to the requirements and constraints of the embodiment.

Two possible side effects of the system described herein are losses in temporal or spatial resolution. That is, during the time spent converging the image, any movement in the image relative to the scanner can necessitate the need to re-converge (increasing latency) and/or can result in indeterminate spot values (effectively decreasing spatial resolution) corresponding to edges having high contrast relative to detector dynamic range. One approach to overcome this issue is to increase frame rate and/or spatial resolution sufficiently to make any indeterminate spots so fleeting or small as to render them insignificant. Another technique may be understood by referring back to FIG. 2, where optional intra-frame image processor 210 and optional inter-frame image processor 216 may cooperate to speed convergence.

As indicated above, optional intra-frame image processor 210 includes line and frame-based processing functions to manipulate and override imager control and can accelerate convergence and extend system sensitivity. Specifically, to control source power levels, optional intra-frame image processor 210 may load grayscale values into the frame buffer to override values that would normally be loaded by inverted residual addition. The intra-frame image processor 210 can also load values to other pixels in the frame buffer beyond the currently processed pixel.

Figure 7:
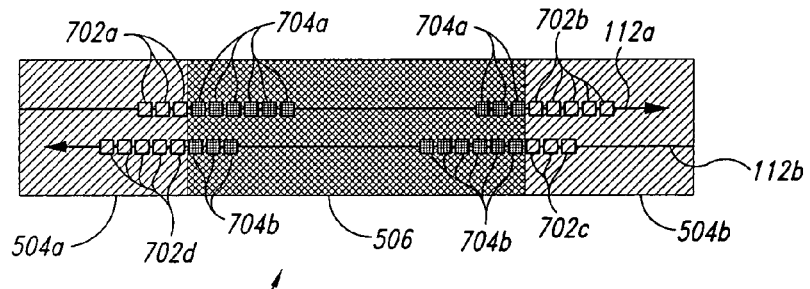
FIG. 7 is a diagram indicating a non-converged state for two exemplary beam scans across an idealized 2D FOV.
Figure 8:
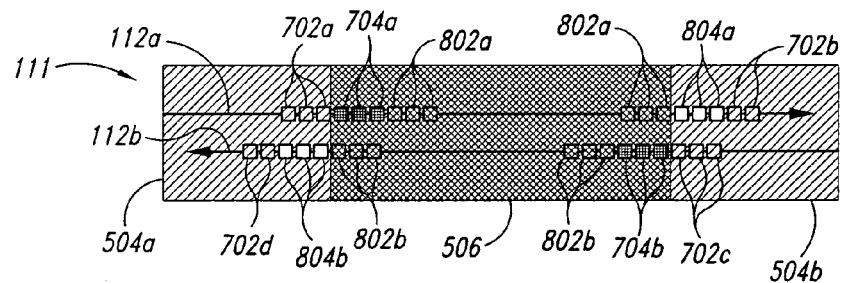
FIG. 8 is a diagram indicating partial intra-frame convergence for the two beam scans of FIG. 7 achieved by using image processing.
Figure 9:
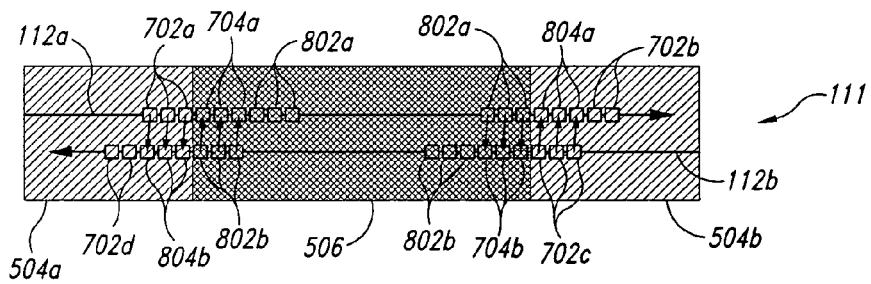
FIG. 9 is a diagram indicating a pseudo-converged state for the two beam scans of FIGS. 7 and 8 achieved intra-frame using further image processing.

FIGS. 7, 8, and 9 illustrate methods used by optional intra-frame image processor 210 and optional inter-frame image processor 216 to increase the rate or decrease the time for convergence with FIG. 7 showing operation corresponding to one frame of the process of FIG. 5. FIG. 7 shows two neighboring scan lines 112a and 112b across 2D FOV 111. In this example, scan line 112a is a left-to-right scan line while scan line 112b is a right-to-left scan line. FOV 111 comprises three regions; a medium gray region 506 abutted on each edge by light gray regions 504a and 504b across which scan lines 112a and 112b pass. Superimposed over the scan lines are individual pixels 702 and 704. Only a few of the pixels are shown for clarity. The areas of interest for this discussion are the few pixels in each scan line corresponding to the transitions from light gray to medium gray and back again. The shading of the pixels indicates the calculated or indeterminate gray values determined by the scanned beam imager. For this discussion, it is assumed that illuminator power for scan lines 112a and 112b is initially set at constant value 509.

Comparing FIG. 7 to FIG. 5, pixels 702a, 702b, 702c, and 702d corresponding to light gray regions 504 are determinate on the first pass as were gray level 00 regions in FIG. 5. Thus, pixels 702 are illustrated as light gray equal to the actual gray level of the corresponding FOV spots. As scan line 112a proceeds from left to right across the transition from region 504a to region 506, pixels 704a corresponding to the right side of the edge are illustrated as black. This indicates their value to be indeterminate. That is, the detector receives a signal below its minimum sensitivity or floor so it is indeterminate if the actual gray level of region 506 is a little darker than the dynamic range of the detector will detect or if it is a lot darker. Proceeding farther along the scan line, all pixels corresponding to spots in region 506 are indeterminate during the current frame (although, per FIG. 5, the illumination power would be reduced for those spots on the subsequent frame and pixels 704a would then become determinate). As the scan line 112a crosses the edge from region 506 to region 504b, it again receives enough optical energy for the signal to be within the range of the detector and thus pixels 702b are determinate and are shown shaded light gray in correspondence with the shading of spots within region 504b. The situation is repeated on subsequent right-to-left scan line 112b, with pixels corresponding to regions 504a and 504b being determinate and pixels corresponding to region 506 indeterminate (dark).

FIG. 8 illustrates a technique for achieving faster convergence for some spots. The technique of FIG. 8 results in some indeterminate (dark) pixels becoming determinate prior to the subsequent frame. A side effect is that it creates some other indeterminate (light) pixels. The particular sign, light vs. dark, of the additional indeterminate pixels is not significant; they are functions of the particular example of FIG. 8. As in FIG. 7, scan line 112a produces determinate light gray pixels 702a corresponding to spots in region 504a. As before, pixel values become indeterminate 704a pixels after crossing the edge from region 504a to region 506. This time, however, an adaptive illuminator power is used to regain determinism while the beam is still within region 506. After one or more pixel values become indeterminate (dark), illuminator power is increased until detected energy again rises above the lower limit of the detector, thus producing determinate medium gray pixels 802a. As the scan line crosses the edge from region 506 to 504b, subsequent pixels 804a are indeterminate (light). This may be caused by the illuminator power being set at a level appropriate to darker region 506, resulting in excess signal from lighter region 504b swamping the detector. In a manner analogous to what happened after the scan path crossed the edge from region 504a to 506, illuminator power is decreased until reflected energy is again within the dynamic range of the detector, resulting in determinate light gray pixels 702b. This process is repeated during subsequent scan 112b.

From inspection of FIG. 8, it can be seen that three indeterminate pixels were produced after an edge of excessive dynamic range was crossed. Thus, in this example, the logic of optional intra-frame image processor 210 required three successive indeterminate (dark) or indeterminate (light) pixels be acquired before resetting the illumination power higher or lower, respectively. Setting a relatively large number of indeterminate pixel acquisitions of the same sign prior to illuminator power adjustment may be useful when detector dynamic range is small relative to FOV dynamic range and/or when relatively high frequency, small features relative to imager addressability are present in the FOV. This can reduce any tendency for the acceleration process to induce instability. A smaller number of indeterminate pixel acquisitions may be more appropriate when features are larger or when the dynamic range of the detector is greater. A further refinement and preferred embodiment automatically sets the gain of the convergence accelerator based upon observed and/or historical FOV attributes such as apparent feature size distribution and apparent dynamic range.

The illuminator power adjustment step size is generally a function of detector dynamic range and the convergence algorithm. For instance, it is generally preferable for small dynamic range detectors for the initial illuminator adjustment to be no greater than the dynamic range of the detector. For images having large features and/or large dynamic range (relative to detector dynamic range), it may be advantageous to have a variable illuminator control step size, larger steps being taken to speed intra-frame convergence. Numerous search algorithms are known and may be applied.

For the case where detector dynamic range is relatively large compared to the apparent dynamic range of the FOV, it may be advantageous to dynamically adjust the illuminator power to keep the scattered signal centered within the dynamic range of the detector. This can increase the system's immunity to loss of convergence when crossing edges.

As an alternative to selecting an initial illuminator power to a constant value, an initial power pattern, for instance embodied as a bitmap in a frame buffer, having variable output may be employed. Especially when detector dynamic range is very limited this may help to speed convergence in scenes having generally large features. This works as a pre-loaded search algorithm comprising illuminator power diversification.

FIG. 9 illustrates a method for accelerating convergence that overcomes the side effect of the additional indeterminate (light) pixels 804a and 804b of FIG. 8. The technique of FIG. 9 makes use of a characteristic of many images that neighboring spots within given regions tend to have similar grayscale values. In particular, spots along one side of an edge tend to have grayscale values similar to neighboring spots along the same side of the edge. Along the opposite side of the edge, the converse is true. Therefore, it is reasonable to use the determinate light gray value of pixels 702a as reasonable guesses of the indeterminate values of pixels 804b. Similarly, grayscale values of pixels 802b may be substituted for indeterminate values of pixels 704a, determinate values of pixels 802a for indeterminate pixels 704b, and determinate values of pixels 702c for indeterminate pixels 804a. FIG. 9 illustrates this approach as arrows pointing from determinate pixels to their associated indeterminate pixels. This procedure may be carried out after scans 112a and 112b to fill in unknown values and create a pseudo-converged image to be verified during the subsequent frame. A similar procedure may also be carried out a priori, using the illumination map of one scan line as the starting point for the illumination map of the subsequent line. Over a period of lines, edges begin to emerge, further informing the image processor(s) of likely values for yet-to-be-scanned pixels in the frame. Edge finding and other applicable algorithms are known to those having skill in the art of image processing and may be applied as is advisable for the application.

As an alternative to feedback or feed-forward control of illuminator power, as described above, or as an alternative implementation of such control, a system may select illuminator power according to one or more illuminator power masks. For the case of a forward-looking colonoscope, for example, the center of the FOV may often be aligned with more distant features than the periphery of the FOV. In such a case, it may be advantageous to use a "center-boost" mask to select higher illuminator power in one or more channels for areas near the center of the FOV. Similarly, angular sensitivity variations of the detector(s) or detector fibers, the distribution of detectors or detection fibers, and other effects may make light gathering less efficient at certain portions of the FOV. A "collection-boost" mask may be used to select higher illuminator power at FOV locations corresponding to reduced collection efficiency.

Illuminator power masks may be fixed, which may be appropriate, for example, when used to overcome collection efficiency variations or when used in specific applications that have repeatable image properties. Alternatively, illuminator power masks may be user selectable, which may be appropriate, for example, when a surgeon wants to momentarily illuminate a distant region. Illuminator power masks may also be automatically selected according to application or image characteristics. Such automatic selection of an illuminator power mask can help to reduce requirements for image processing horsepower by reducing or eliminating the need to process feedback (or feed-forward) algorithms or look-ups on a pixel-by-pixel basis.

Referring back to the FIG. 2 discussion of probing dark and/or distant spots in conjunction with the foregoing discussion of FIG. 9, a way to improve convergence time of such distant spots may be seen. Because surrounding pixels have a reasonable probability of similar gray values, the system can determine a reasonable initial set of pixel values for rapid convergence by applying probe bursts sparsely across a region, and selecting intervening pixel values by interpolation between determinate values. Over a period of several frames, the system may eventually probe all pixels in dark regions to provide complete FOV grayscale information not otherwise obtainable. To prevent overexposure to laser light, the rule set and burst approach is defined with care.

Optional inter-frame image processor 216 performs frame-based image processing and may be used to inform the system of edge tracking and probing functions, as well as converting the frame buffer values to values appropriate for display or further processing. Optional inter-frame image processor 216 may include image de-skewing to compensate for a moving FOV, white balance compensation, gamma correction (grayscale expansion, compression, or shifting), gamut correction (gamut expansion, compression, or shifting), pixel interpolation, suppression of non-valid pixel values, noise reduction, and combining frame buffer and detector data.

Many of the optional inter-frame image processor 216 functions are based upon edge finding and tracking techniques such as gradient or Sobel operators for edge finding and local maximum/minimum feature extraction for tracking. These and other techniques for edge finding and local maximum/minimum feature extraction are known to those having skill in the art of image processing. Also, as optional intra-frame image processor 210 operates, it may leave indeterminate values in the frame buffer. Optional inter-frame image processor 216 can "scrub" these from the output by tracking which pixels are indeterminate and optionally combining this data with other FOV information.

When several edges have identical movement vectors, optional inter-frame image processor 216 can infer overall FOV movement relative to the system and calculate resulting skew and perform de-skewing algorithms.

White balance processing can compensate for differences in source efficiency or power as well as differences in detector efficiency. Stored calibration values make this process fairly straightforward. To simulate ambient illumination effects, optional inter-frame image processor 216 may shift values to an effective illumination color temperature.

Optional inter-frame image processor 216 may reduce noise using noise correlation principles to distinguish between variations in frame buffer data related to structure in the scene and noise artifacts, and can apply a smoothing function to "clean up" the image. Techniques for doing this are known to the art.

Figure 10:
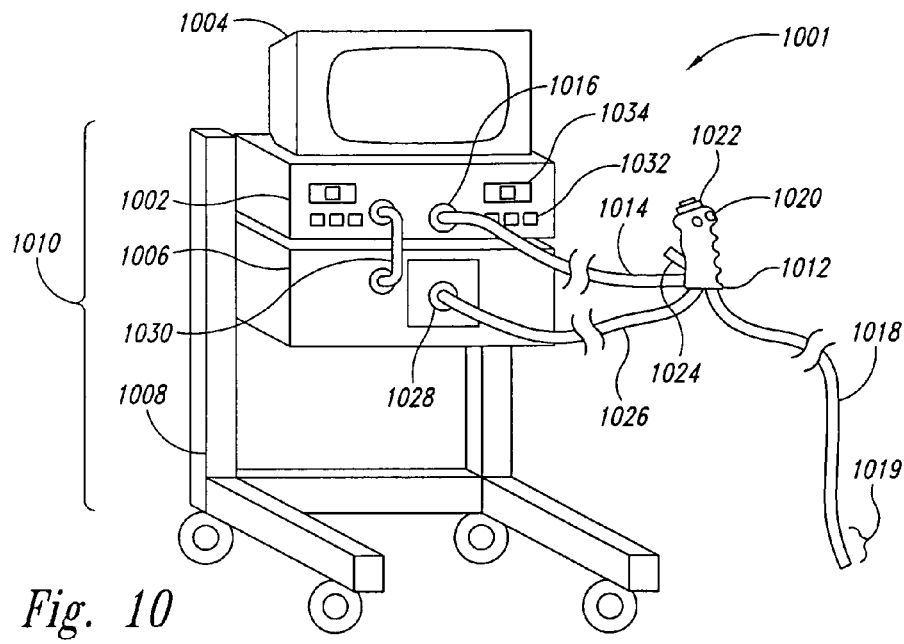
FIG. 10 is an isometric drawing of an endoscope system.

FIG. 10 is an isometric drawing of an endoscope system. Control module 1002, monitor 1004, and optional pump 1006 may be mounted on a cart 1008. Taken together, these modules may be referred to as console 1010. Items comprising 1010 may optionally be mounted separately or may be combined as appropriate for the application. Console 1010 communicates with hand piece 1012 through external cable 1014, which is connected to console 1010 via connector 1016. Connector 1016 has two parts 1016a and 1016b (not shown for clarity) that may be coupled and decoupled. Hand piece 1012 is connected to endoscope tip 1018, which may be of a flexible type or a rigid type (typically referred to as a laparoscope). Distal tip 1019, which may for example be a steerable tip, includes means for scanning a beam over a field-of-view, collecting the scattered light energy, and sending a signal representative of the scattered light energy back up through endoscope 1018, hand piece 1012, and external cable 1014 into console 1010.

Hand piece 1012 may include optional controls 1020, which may for example include brightness, zoom, still photo, FOV angle, tip wash, irrigate, lubricant dispense, and other inputs that are advantageous to have immediately accessible to the user. Additionally, when endoscope 1018 is of a flexible type, hand piece 1012 may include steering controls 1022 that control the angle of the distal tip 1019 makes with respect to the rest of endoscope 1018. Hand piece 1012 may further include working channel fitting 1024, into which may be inserted various tools that may be threaded down the working channel of endoscope 1018, emerging substantially at the end of the distal tip 1019 to perform various surgical, diagnostic, or other tasks.

Optional pump 1006 may include a separate irrigation hose 1026 that connects to hand piece 1012. Irrigation hose 1026 may be connected to optional pump 1006 via connector 1028. Solution pumped through irrigation hose 1026 is from there forced into the optional irrigation channel of endoscope 1018. Alternatively, optional pump 1006 may include a shunt hose 1030 that connects to control module 1002, fluids carried by shunt hose 1030 thereafter being combined with other signal lines within control module 1002 to be sent to the hand piece 1012 and on to the endoscope 1018 via connector 1016 and external cable 1014. This optional arrangement results in fewer external hoses and cables to get in the way of the user.

As an alternative or in addition to pump 1006, suction may be applied for removing unwanted fluids and debris from the working space.

Console 1010 may also include additional controls 1032 and/or indicators 1034, here shown as being on control module 1002. These controls and indicators may, for example, be of a type that are useful when setting up or troubleshooting the apparatus of FIG. 10.

Figure 11:
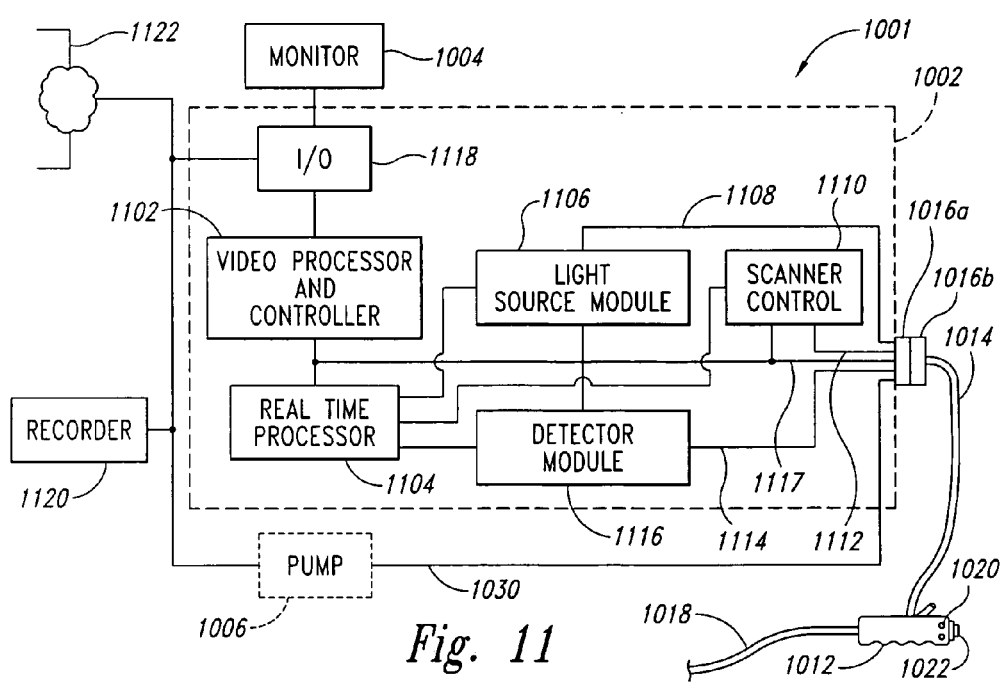
FIG. 11 is a block diagram emphasizing relationships between various components of an endoscope system.

FIG. 11 is a block diagram emphasizing relationships between various components of an endoscope system. Control module 1002 contains several logical and/or physical elements that cooperate produce an image on monitor 1004. Video processor and controller 1102, which may be in the form of a microcomputer main board, receives control inputs and controls the operation modes of the other elements within control module 1002. Additionally, video processor and controller 1102 may include image processing functions.

Real time processor 1104, which may for example be embodied as a PCI board mounted on video processor and controller 1102, may alternatively be a logical device that is physically one with video processor and controller 1102. Real time processor 1104 interacts with light source module 1106, scanner control module 1110, and detector module 1116. Light source module 1106, which may alternatively be housed separately, includes one or more illuminators that create the light energy used for beam scanning by the imaging tip. Light source module 1106 outputs light energy via optical fiber 1108, which, in turn, connects to external cable 1014 via connector 1016, here depicted as having two sections 1016a and 1016b. After passing through hand piece 1012 en route to endoscope 1018 and being scanned across the FOV, light is collected at the endoscope tip and a representative signal returned back up through endoscope 1018, hand piece 1012, and external cable 1014, through connector 1016 and back into the controller module 1002.

In some embodiments, the representative signal passed back up through the external apparatus is sent as an optical signal. Thus return signal line 1114 may be a fiber optic cable or bundle of fiber optic cables that are routed to detector module 1116. At detector module 1116, the optical signals corresponding to the FOV characteristics are converted into electrical signals and returned to the real time processor 1104 for real time processing and parsing to the video processor and controller 1102. Electrical signals representative of the optical signals may be amplified and optionally digitized by the detector module 1116 prior to transmission to real time processor 1104. Alternatively, analog signals may be passed to real time processor 1104 and analog-to-digital conversion performed there. Detector module 1116 and real time processor 1104 may be combined into a single physical element.

In alternative embodiments, light representative of the FOV may be converted into electrical signals at the tip by one or more photo-detectors such as photodiodes, for example. In this case, return line 1114 may be embodied as electrical wires and detector module 1116 may be omitted. In the case where distal optical to electrical conversion is performed, it may be advantageous to amplify the detected signals in the imaging tip as well to reduce impedance, reduce electrical noise, and improve the responsivity of the detector or detectors. Additionally, it may be desirable to perform analog-to-digital conversion at the distal imaging tip 1019, or alternatively in the hand piece 1012 in the interest of reducing impedance of the relatively long signal lines that pass through external cable 1014, hand piece 1012, and in the case of distal tip A/D conversion, endoscope 1018. In this case signal lines 1114 may comprise digital lines and connector 1016 a connector for coupling at least certain digital signals.

Real time processor 104 may optionally perform signal leveling, modulating light source module output in response to the apparent brightness of each spot in the FOV.

Scanner control module 1110 controls the beam scanner in the imaging tip. In the case of a scanner having integral position sensing, it may also process sense lines indicative of scanner position. Thus scanner control lines 1112 may include bidirectional control lines. Scanner control module 1110 may directly provide scanner drive current. Alternatively, it may provide a signal representative of desired scanner drive with conversion to drive current being performed at a more distal region such as the hand piece 1012 or imaging tip 1019. In this case as well as other alternatives, it may be desirable to provide DC or AC power from console 1010 through connector 1016 and into the distal assembly.

As an alternative or adjunct to determining scanner position from scanner control lines 1112, it may be advantageous to determine scanner position from the FOV representative signal passing through return signal lines 1114. In this case, real time processor 1104 may drive scanner control module 1110 in a manner responsive to the received optical signal.

The scanner may be driven from control module 1002, or alternatively the system may use the actual scanner frequency to drive the system, colloquially referred to as "tail-wags-dog".

Additionally, control lines 1117 may be passed to hand piece 1012 for input of control signals via user operation of controls 1020 and optional steering controllers 1022. When steering is performed under console control rather than strictly from a physical connection between steering controllers 1022 and control wires, control lines 1117 may additionally carry control signals outbound to control steering means. Control lines 1117 may additionally carry indicator or display information to the hand piece 1012 for transmission to the user.

Video processor and controller 1102 has an interface 1118 that may comprise several separate input/output lines. A video output may run to monitor 1004. A recording device 1102 may be connected to capture video information recording a procedure. Additionally, endoscopic imaging system 1001 may be connected to a network or the Internet 1122 for remote expert input, remote viewing, archiving, library retrieval, etc. Video processor and controller 1102 may optionally combine data received via I/O 1118 with image data and drive monitor 1004 with information derived from a plurality of sources including imaging tip 1019.

In addition to or as an alternative to monitor 1004, the display may be output on one or more remote devices such as, for example, a head mounted display. In that event, context information such as viewing perspective may be combined with FOV and/or other information in video processor and controller 1102 to create context-sensitive information display.

Pump 1006 may have its control lines fed from handpiece 1012 through control module 1002. FIG. 11 illustrates the case where irrigation is run into the control module via irrigation shunt 1030 and out through connector 1016.

Not shown are additional optional features such as a lubricant, saline, and/or anesthetic pump.

Figure 12:
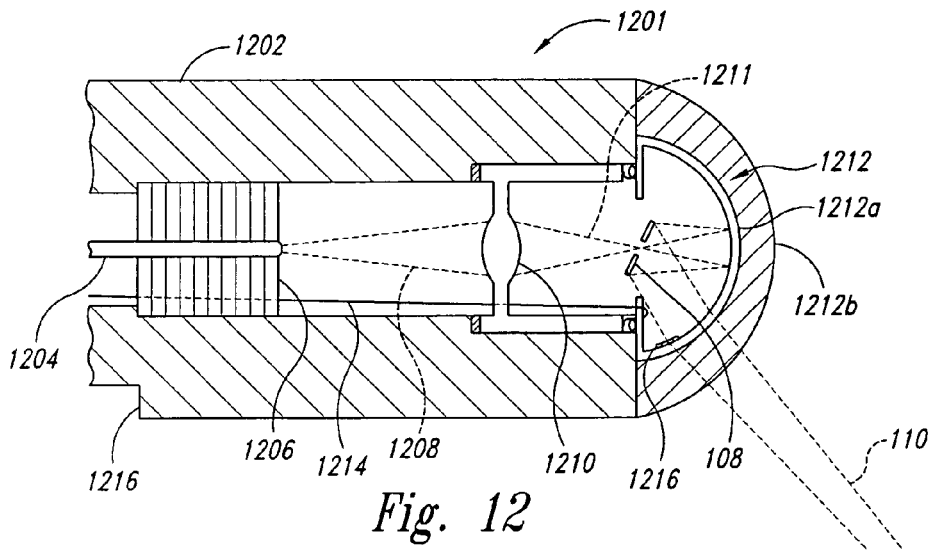
FIG. 12 is a side sectional view of a scanning tip module.

FIG. 12 is a side sectional view of a scanning module 1201. The scanning module is comprised of a housing 1202 that encloses and supports the scanner 108 and associated mechanism. Optical fiber 1204, which may for example be a single mode optical fiber feeds light to the scanning module and is affixed to housing 1202 by a ferrule 1206. The end of optical fiber 1204 may be polished to create a known divergence angle of raw beam 1208. Raw beam 1208 is shaped by beam shaping optic 1210 to create a beam shape appropriate for transmission through the rest of the system. As shown, all or a portion of beam shaping optic 1210 may be moveable or deformable to control beam divergence, waist position, and waist angle. After shaping, shaped beam 1211 is fed through an aperture in the center of the MEMS scanner 108, is reflected off a first reflecting surface back onto the front of the scanner, and then out of the scanning module as scanned beam 110.

As an alternative to or in addition to beam shaping optic 1210, a reflective beam shaping optical element, optionally combined with the scan mirror 108, may be used. Such a device is taught in U.S. patent application Ser. No. 09/400,350, entitled OPTICAL SCANNING SYSTEM WITH CORRECTION, filed Sep. 11, 2000 by Clarence T. Tegreene and David Dickensheets, commonly assigned herewith and hereby incorporated by reference.

In some embodiments of FIG. 12, a dome 1212 is affixed to the end of housing 1202. Dome 1212 provides a number of functions. The inside of dome 1212 includes the first reflecting surface, here shown as integral to the entire inside of the dome. Alternatively, the first reflecting surface may be suspended between the dome and scanner or the first reflecting surface may be formed as a specific feature of the dome such as a protruding pillar with reflective end. As shown, the inside surface of the dome provides the first reflecting surface. Additionally, the inside and/or outside of the dome may have optical power and thus further shape the beam as it passes through to become scanning beam 110. Additionally, dome 1212 may provide a hermetic seal with housing 1202, thus protecting optical elements inside from contact with the environment.

Control and/or power leads 1214 pass through ferrule 1206. Leads 1214 connect to scanner 108, providing the drive signal and, optionally, position feedback. Mirror position may be determined using doped piezo-resistive elements as described in one or more of the MEMS scanner patents incorporated by reference. Electrical leads 1214 may also include control and feedback connections for controlling focus characteristics of beam shaping optic 1210.

Alternatively, mirror position may be determined optically. Sensing element 1216 may for instance be used to detect one or more ends of scan, thus providing synchronization information. Sensing element 1216 may for example be a photodiode that sends a signal to the console 1010, and specifically to scanner control module 1110, when it is struck by scanned beam 110. Alternatively, sensing element 1216 may be an optical element of known reflectivity that sends a retro-collected optical signal back up the beam path and through optical fiber 1204. In this case, a beam-splitter, evanescent coupler, or equivalent element may be incorporated in light source module 1106 to pick off the returned signal for detection and transmission to other control elements such as real time processor 1104.

Registration notch 1216 may be formed in housing 1202 to aid in registering scanning module 1201 to scanning tip 1019.

Figure 13:
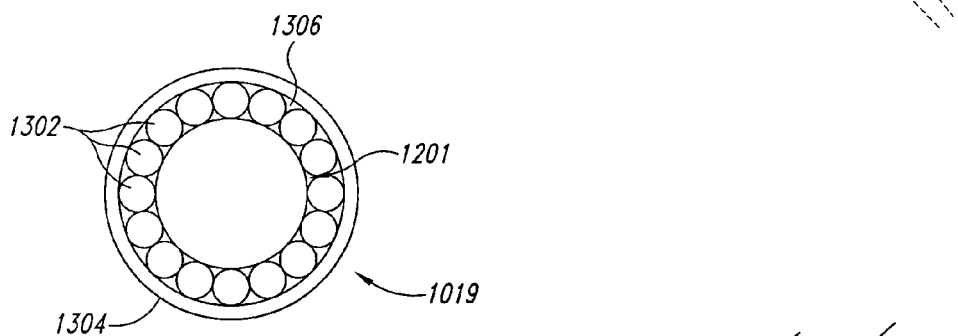
FIG. 13 is a cross sectional view of a scanning endoscope imaging tip.

FIG. 13 is a cross sectional view of a scanning endoscope distal imaging tip 1019. Scanning module 1201 is surrounded by detector elements 1302, which are in turn surrounded by outer sheath 1304. Detector elements 1302 may for example be multi-mode optical fibers that transmit the reflected signal back up distal tip 1018 and on to detector module 1116 in controller 1002. Interstitial spaces 1306 may be present among detector elements 1302.

As an alternative to fiber optics, detector elements 1302 may comprise optical-to-electrical converters such as photodiodes, for example. Outer sheath 1304 may be flexible in the case of a flexible endoscope or alternatively may be rigid in the case of a rigid laparoscope or equivalent rigid device. As an alternative, outer sheath 1304 may be inserted into another body that acts as the actual outer covering of the device.

Figure 14:
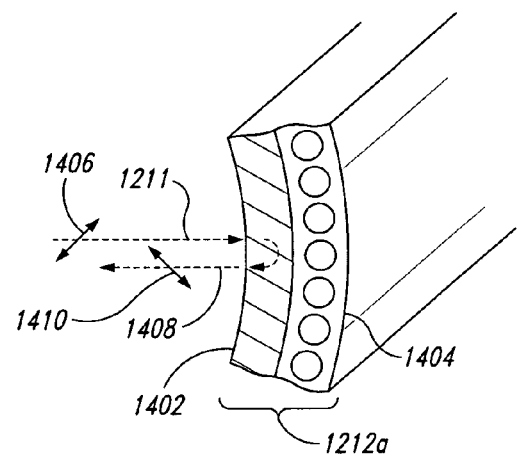
FIG. 14 is a side sectional view of an embodiment of the inner dome surface of a scanning tip module having differential reflection of two polarizations of light.

FIG. 14 is a side sectional view of an embodiment of a inside dome surface of a scanning tip module having differential reflection of two polarizations of light. Inner surface 1212a may be comprised of two layers, a quarter wave rotator 1402, and a reflective polarizer 1404. Reflective polarizers often include sub-wavelength spaced parallel conductors that allow the polarization parallel to their orientation to pass while reflecting the polarization component perpendicular to their orientation. An example of such a polarizer is disclosed in U.S. Pat. No. 6,449,092, entitled REFLECTIVE POLARIZERS HAVING EXTENDED RED BAND EDGE FOR REDUCED OFF AXIS COLOR, hereby incorporated by reference.

When incident shaped beam 1211, having a particular polarization 1406 passes through quarter wave plate 1402, its polarization is rotated 45°. In a preferred embodiment, it is rotated to be perpendicular to the transmissive axis of reflective polarizer 1404. It thus is reflected back as beam 1408 through quarter wave plate 1402, rotating its polarization another 45° to a polarization 1410 perpendicular to incident polarization 1406. Reflected beam 1408 then reflects off scanner 108 (not shown), becoming scanning beam 110.

Reflective polarizer 1404 may cover only a portion of the inside of dome 1212 corresponding with incident light from beam 1211. Alternatively, the entire inside of the dome may be covered with reflective polarizer 1404. For those cases where scanning beam 110 again encounters reflective polarizer 1404, it first has its polarization rotated 45° as it passes through quarter wave plate 1402 a third time. This time, the polarization of scanning beam 110 is rotated to be parallel to the transmissive axis of reflective polarizer 1404, and thus passes through dome 1212.

As mentioned above, a semi-transparent mirror may be substituted for the reflective polarizer and other polarization-related structures.

Figure 15:
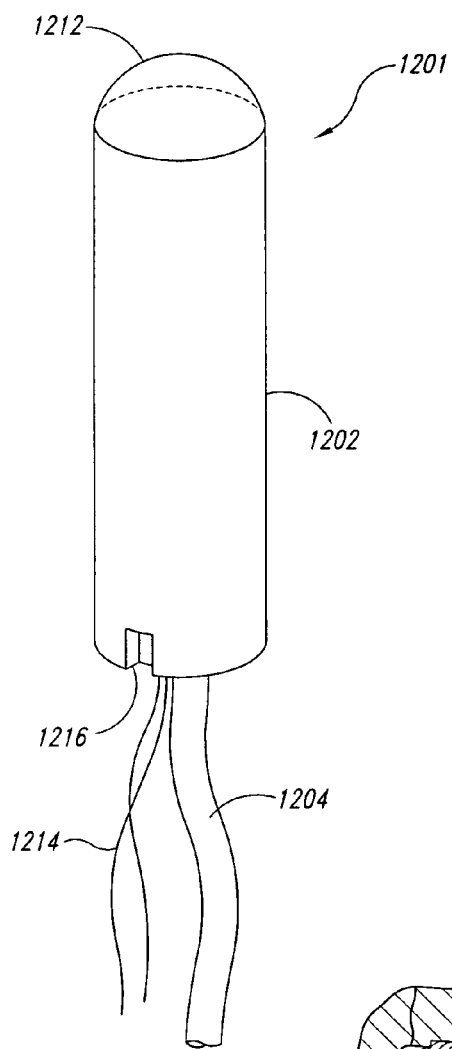
FIG. 15 is an isometric view of a scanning module.

FIG. 15 is an isometric view of scanning module 1201 showing a tubular housing 1202 with a dome 1212 affixed to the distal end. Scanning module 1201 also includes registration notch 1216 formed in the proximal end housing 1202, as well as optical fiber 1204 and electrical leads 1214 emerging from the proximal end of scanning module 1201. Scanning module 1201 may for example have an outer diameter of about 2.5 mm or less and a length of about 20 mm or less.

Figure 16:
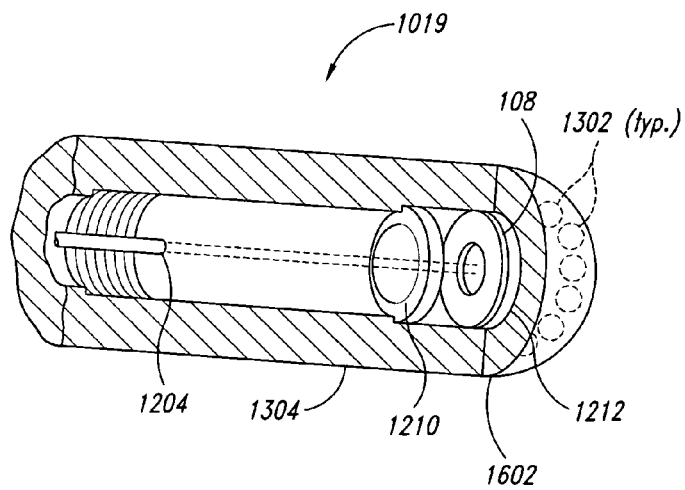
FIG. 16 is an isometric view of the optical elements of an imaging tip.

FIG. 16 is an isometric view of the optical elements of a distal imaging tip 1019 giving the reader a better perspective of the relative placement of scanning module features shown in FIG. 12 and light detection elements 1302 embodied as optical fibers. Coupling element 1602 may be used to improve the mechanical robustness of the detector fibers and/or increase the effective numerical aperture of the optical fibers 1302 and provide more efficient gathering of scattered or reflected light. For embodiments where the high index cores of the detector fibers are relatively soft, a transparent material such as a plastic or glass may be used for element 1602 to hold the cores in place. In other embodiments, it may be advantageous to use a material that improves the N.A. of the detection fibers 1302. Such an N.A. enhancing element may be advantageous for gathering light from the periphery of a large FOV such as a 120° to 140° FOV, for example. For this application, various materials known to the art may be used such as, for example poly-tetra-fluoro-ethylene (PTFE) or other materials with similar optical properties.

In some embodiments, coupling element 1602 may include a polarizer cross-polarized to the scanning beam 110 (not shown). Such a polarizer may help to reject specular reflections in the field-of-view, thus reducing glints that may hinder image quality.

In this embodiment, the entire assembly is surrounded by outer sheath 1304.

Figure 17:
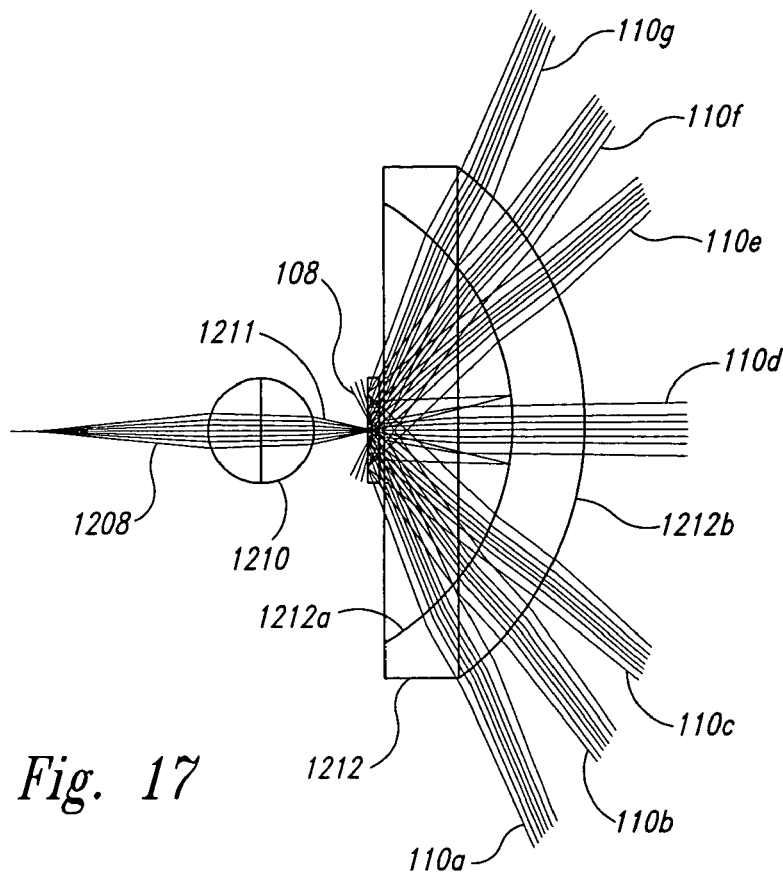
FIG. 17 is a ray trace of a distal tip optical design similar to that depicted in FIGS. 12-16.

FIG. 17 is a ray trace of a distal tip optical design similar to that depicted in FIGS. 12-16. Input beam 1208 is shaped by ball lens 1210 to pass through the aperture in MEMS scanner 108 (here shown in several discrete positions), after which it reflects from the inside surface 1212a of dome 1212 back onto the mirror 108. Several positions of scanning beam 110 are shown as beams 110a through 110g. The scanning beam passes through dome 1212 where it is shaped by both the inside surface 1212a and outside surface 1212b to create the beam shape indicated by the rays of scanning beam positions 110a through 110g.

Figure 18:
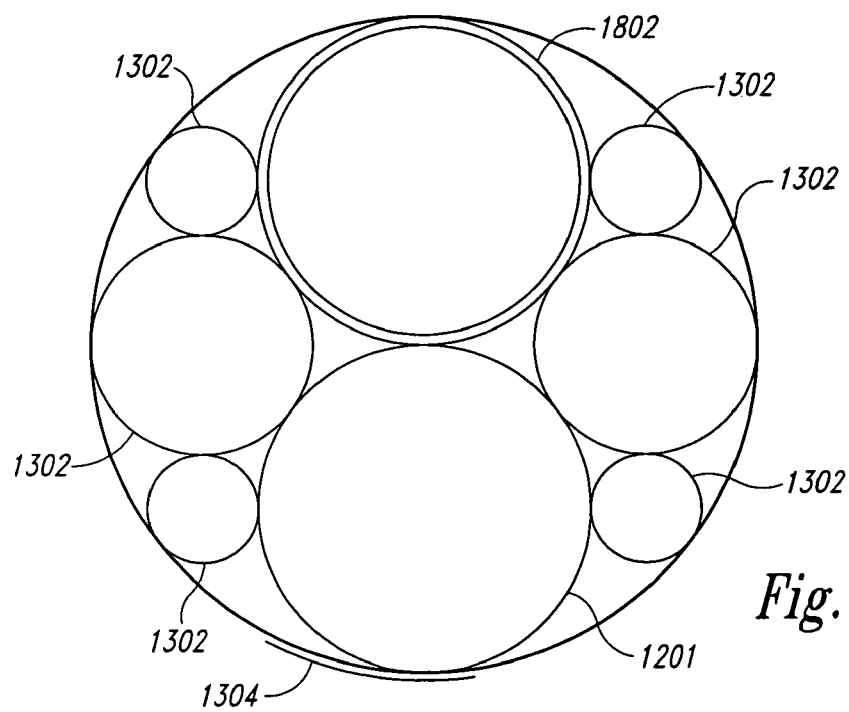
FIG. 18 is a tip layout that includes detection fibers arranged in interstitial spaces around a scanning module and a working channel.

FIG. 18 is a tip layout that includes a working channel and detection fibers arranged in interstitial spaces around the scanning module and working channel. Outer sheath 1304 encloses a scanning module 1201 and a working channel 1802. Working channel 1802 is disposed to pass surgical tools, diagnostic tools, or fluids such as air for inflation, saline for irrigation, or in vivo fluids for removal and disposal. In other embodiments, channel 1802 or one or more of detection fibers 1302 can be substituted by a lubricant delivery or drug delivery channel. The tip layout of FIG. 18 is amenable to both rigid laparoscopes and flexible endoscopes.

Of note is the ability of the present invention to distribute the detection elements around the tip in available spaces without regard to maintaining specific orientation relative to the imager.

Figure 19:
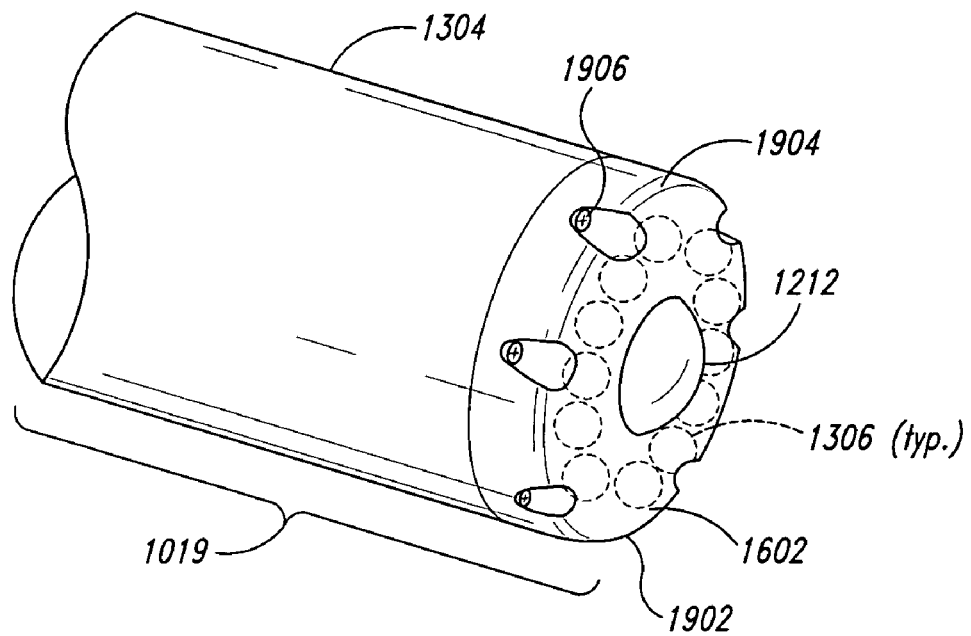
FIG. 19 is an isometric view of a distal tip with lubricant delivery.

FIG. 19 is an isometric view of a distal tip with lubricant delivery. Outer sheath 1304 is capped by end cap 1902, which includes an integral optical coupling plate 1602 and scanning module dome 1212. Return fibers 1306 are indicated as lying behind the integral optical coupling plate portion of end cap 1902. The corners 1903 of end cap 1902 are formed with a radius to ease passage of the endoscope through body tissues while minimizing damage. End cap 1902 further includes at least one lubricant delivery orifices 1906 through which a lubricant may be delivered to further ease passage through body tissues and/or body cavities. Intermittently or continuously, a lubricant may be dispensed from lubricant delivery orifices 1906. Because a significant amount of patient trauma arising from endoscopic procedures is related to forcing the endoscope around bends in the GI system, this lubricant delivery system can reduce patient trauma and discomfort. In one embodiment, lubricant is available on demand by the clinician pushing a plunger at the hand piece to send lubricant down a lubricant tube and out the lubricant delivery orifices 1906. In this embodiment, the lubricant may be stored in a syringe. In another embodiment, the clinician may enable a pump that pumps lubricant out the lubricant delivery orifices. In still another embodiment, the lubricant may be dispensed automatically.

Many lubricants may be used. Water-soluble lubricants such as K-Y jelly may be advantageous for some applications.

Figure 20:
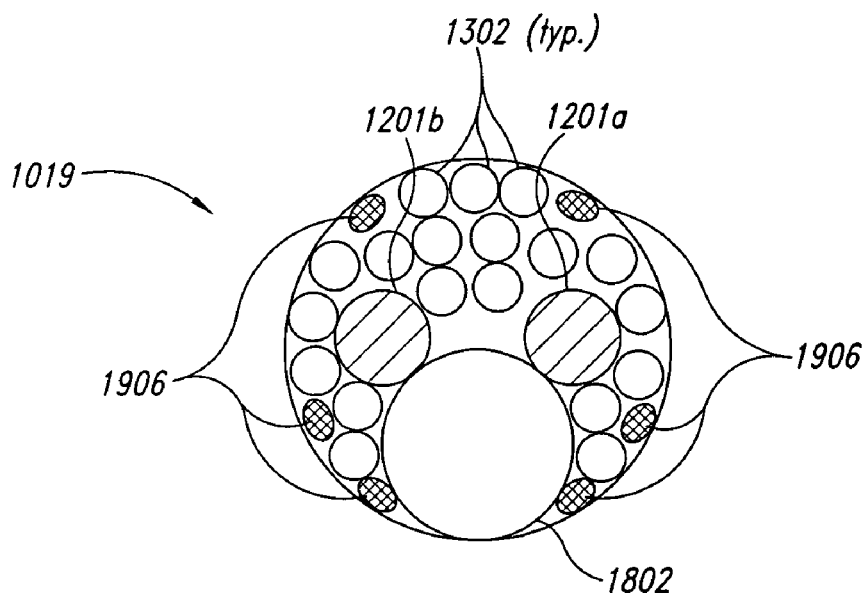
FIG. 20 shows an endoscope tip layout having stereo or binocular imaging capabilities.

FIG. 20 shows an endoscope tip layout having stereo or binocular imaging capabilities. Scanning modules 1201a and 1201b are arranged at perspective locations in the tip so as to create parallax between their respective fields of view. In the embodiment of FIG. 20, they are spread apart on a horizontal chord that defines a "horizon" for viewing. The viewing angle may optionally be inverted if desired. Working channel 1802 is shown exiting between and below the scanning modules. Detection fibers 1302 are arrayed around other features as space allows. In some embodiments, it may be preferred to pack as many detection fibers as possible into the interstitial spaces across the distal tip to maximize return signal strength. Lubricant apertures 1906 are shown arrayed around the periphery of the imaging tip 1019.

In operation beams from scanning modules 1201a and 1201b may be simultaneously or alternately scanned across their respective fields of view, which may be substantially overlapping. If simultaneously scanned, the beams may be encoded to facilitate demultiplexing of the return signals. For instance, wavelengths between the two modules may be offset slightly from one another and optical means used to separate the signals. In another embodiment, the beams may be frequency encoded to facilitate demultiplexing in the electrical domain.

A tip having multiple scanning modules may also be used, for example, to expand the composite field-of-view, to provide a zoom capability, to provide greater resolution, or to scan differing wavelengths of light, among other things. For the case of creating an expanded composite field of view, the fields of view of each respective scanning module may be tiled or slightly overlapped to produce an overall image size larger than that produced by any individual scanning module. Tiling of images is described in greater detail in one or more of the commonly assigned U.S. patents incorporated by reference.

For the case of a plurality of scanning modules providing zoom capability, such a system may be operative continuously, automatically, or selectively. In one example of such a system, a first scanning module may be configured to provide SVGA addressability across a 140° FOV with a matching resolution—that is, with a projected spot size set to substantially match the spacing of the pixels at some working range or range of working ranges. A second scanning module may be configured to provide SVGA addressability across a 70°

FOV at one or more working ranges with a matching resolution. In this case, the second scanning module might be set to scan a spot size one-half the diameter of the first spot size at an equivalent working range. Alternatively, the second scanning module might be configured to scan an equivalent spot size at twice the working range of the first scanning module. Other combinations will be clear to those having skill in the art.

For embodiments using a plurality of scanning modules used to provide greater resolution, several modes exist. In a first mode, the plurality of scanning modules may scan substantially equivalent fields of view, but do so in a way where one scanning module scans spots that are interleaved or interlaced with respect to the spots scanned by other scanning modules. In another mode, the plurality of scanning modules may be configured such that one scanning module scans an area of the FOV of another scanning module that may be sparsely sampled. With resonant MEMS scanners, for example, the scanner has the highest angular velocity at the center of the FOV, a situation that may result in spots being spread out relative to one another near the center of the FOV. It may be desirable for certain applications to have a scanning module that scans the center of the FOV of another scanning module, thus providing greater sampling in that region. In biaxially resonant or Lissajous scanning, it is common to have certain locations in the FOV where sampling is done less frequently than other locations. A plurality of scanning modules may be useful in such a case to provide more frequent sampling of areas infrequently sampled by a particular scanning module.

In another embodiment, one or more scanning modules may be configured to provide hyperspectral imaging, optionally at a different frame rate or with a different FOV than a scanning module used for imaging in visible wavelengths. For example, infrared wavelengths require a larger mirror to achieve similar resolution, but can also tolerate somewhat higher mirror deformation than visible wavelengths. An infrared scanning module may be equipped with a larger mirror that has somewhat higher dynamic deformation than a visible scanning module. Similarly, an ultraviolet scanning module may be equipped with a smaller mirror that has less dynamic deformation than a visible scanning module. In another aspect, certain reflective or transmissive materials may not have properties appropriate for hyperspectral wavelengths. Additional scanning modules may be employed that use materials more properly suited to hyperspectral wavelengths. For example, an ultraviolet scanning module may be equipped with fluorite lenses and UV-optimized reflectors and/or polarizers. An infrared scanning module may be equipped with lenses, reflectors, and/or polarizers optimized for longer wavelengths.

Figure 21:
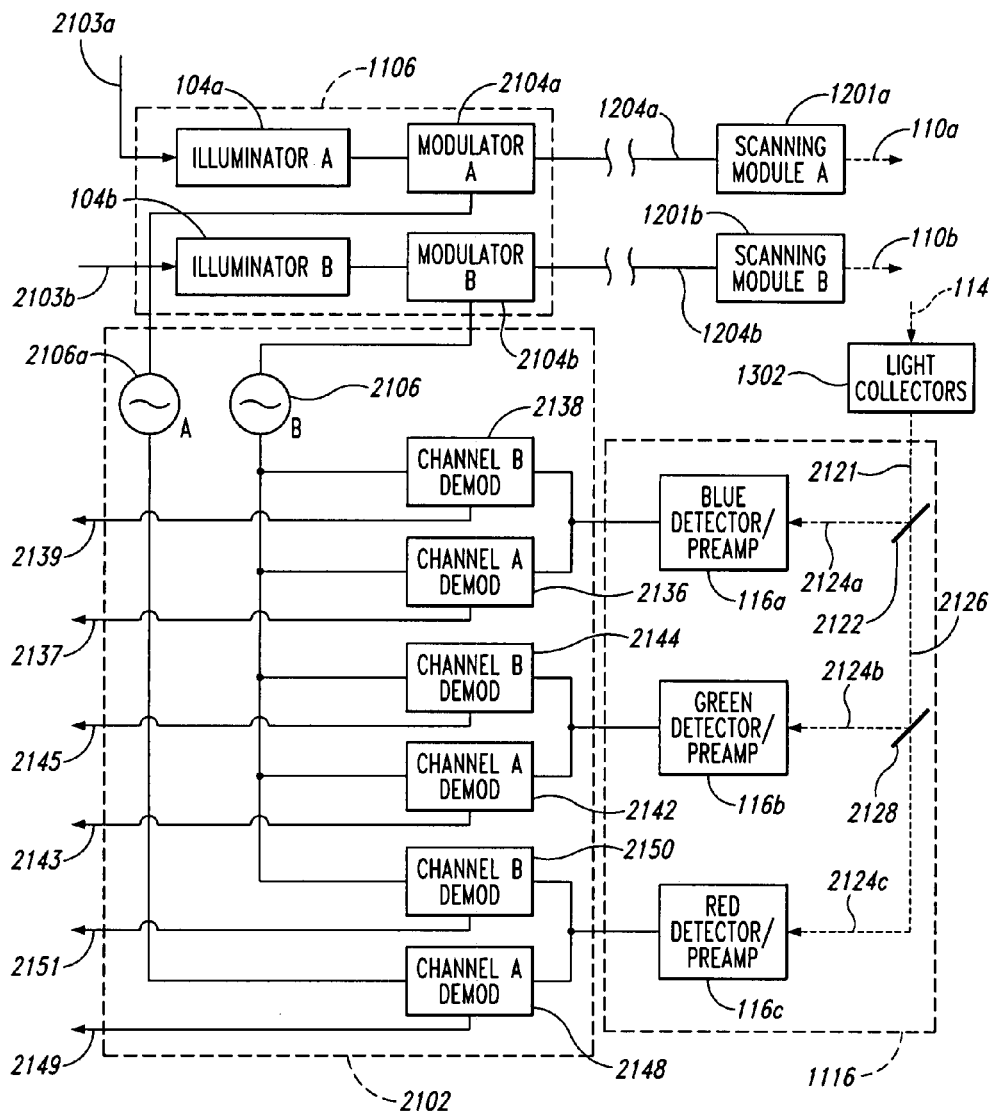
FIG. 21 is a block diagram of a controller for demultiplexing two simultaneously scanning beams.
Figure 22:
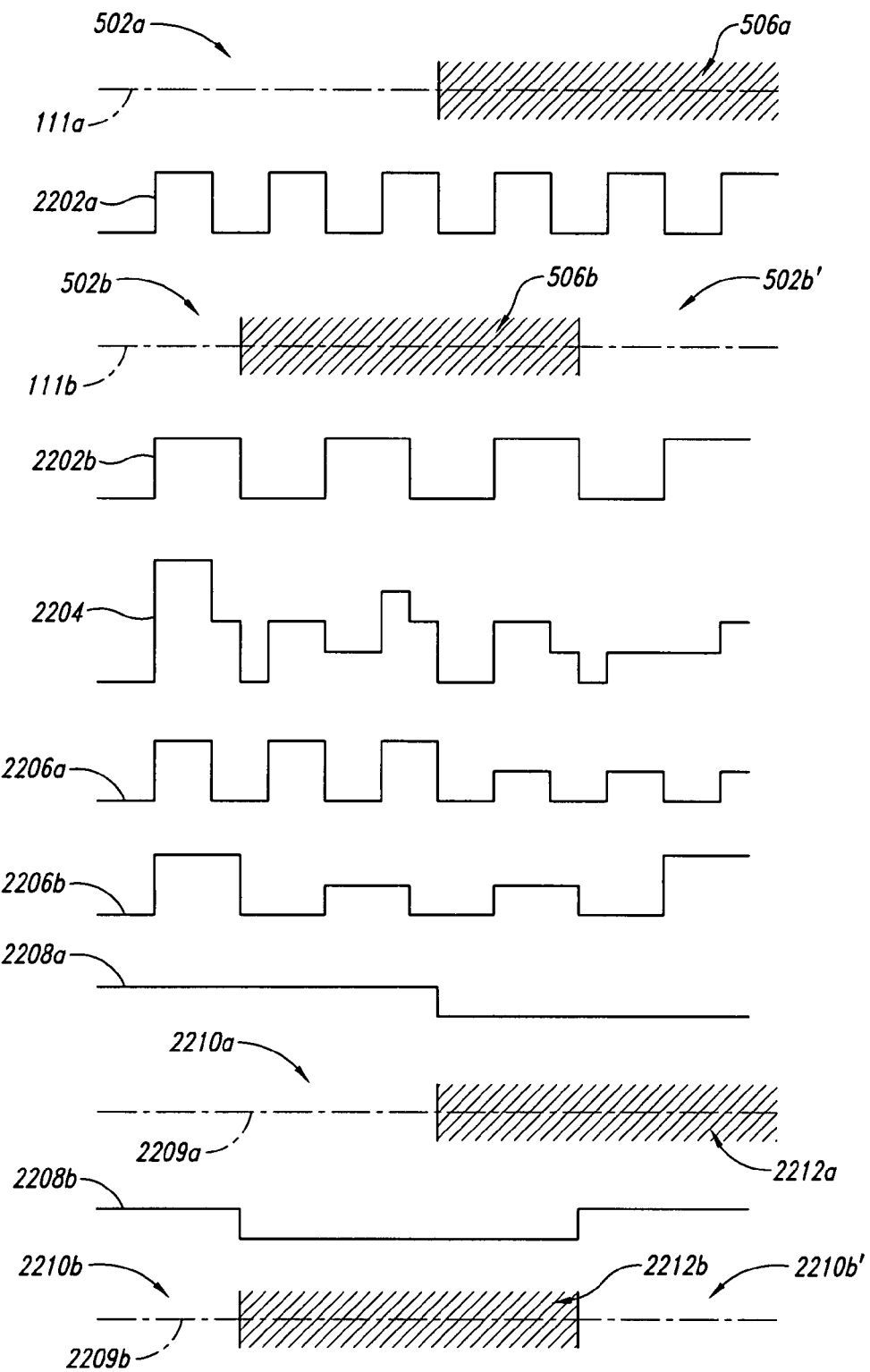
FIG. 22 is a diagram showing the waveforms for a pair of frequency multiplexed beams.

FIG. 21 is a block diagram of a controller for multiplexing and demultiplexing two simultaneously scanning beams. The beams may, for example, be scanned by scanning modules arranged as per the tip layout of FIG. 20. The embodiment of FIG. 21 uses synchronous illumination and detection to separate signals from a plurality of scanner modules 1201, illustrated here as two particular scanner modules 1201a and 1201b. Timer-controller 2102 controls the synchronization of the illuminator channels on light source module 1106 and detector channels on detector module 1116. Functional implications of this and alternative synchronous embodiments are illustrated in FIG. 22.

Embodiments related to FIG. 21 may pulse paired illuminators and detectors synchronously. The detection circuit is "tuned" to the pulse rate of the appropriate illuminator, thus rejecting light produced by non-paired illuminators.

Timer-controller 2102 may comprise a plurality of RF sources 2106a, 2106b, etc. Alternatively, it may generate or use an RF signal that is then used to synthesize individual RF signals 2106a, 2106b, etc.

Light source module 1106 includes a plurality of illuminators 104a, 104b, etc., driven by illuminator drive signals 2103a, 2103b, etc., respectively. Illuminators 104a, 104b, etc. may be modulated by external modulators 2104a, 2104b, etc. or alternatively may be internally modulated. For many applications, Illuminators 104 may comprise a plurality of individual light sources that are multiplexed to form composite illumination, for example red, blue, and green (RGB) lasers whose RGB light is combined to form substantially white light.

RF sources 2106a and 2106b control external modulators 2104a and 2104b, respectively, to modulate the light produced by illuminators 104a and 104b, respectively, as channels A and B, respectively. Modulated illumination channels A and B are sent to the imaging tip via optical fibers 1204a and 1204b, respectively, into Scanning Module A 1201a and Scanning Module B 1201b, respectively. Scanning Modules 1201a and 1201b produce scanned beams 110a and 110b, respectively, each modulated according to the described schema.

Scattered light signal 114 is collected by light collectors 1302. For cases where light collectors 1302 are non-imaging, they cannot spatially distinguish between scattering from scanned spots produced by channels A and B. However, scattered light signal 114 contains a plurality of modulated signals (two in this example), each potentially comprising many wavelengths (three in this example). The modulated signals that may be separated according to their modulation characteristics while the wavelengths may be separated according to their differential response to dielectric mirrors, filters, refraction, etc. Light collectors 1302 transmit the composite scattered optical signal to detector module 1116, which may for example be located remotely from the imaging tip in a console according to FIGS. 10 and 11.

Within detector module 1116, the scattered light signal is separated into its wavelength components, for instance RGB. Composite signal 2121 is split by dielectric mirror 2122 into a first wavelength signal 2124a, which may for instance comprise blue light, and a remaining composite signal 2126, comprising all wavelengths present except substantially for that split into first wavelength signal 2124a. Similarly, a second wavelength, for example green, may be split by dielectric mirror 2128 into a second wavelength signal 2124b and a remaining composite signal 2124c. For the present example, there are only three wavelengths present in scattered signal 114 and composite signal 2121, so remaining composite signal 2124c contains substantially only red light.

The RGB optical signals 2124c, 2124b, and 2124a, respectively, are each fed to associated photo-detectors and amplifier circuits, 116c, 116b, and 116a, respectively. Within the detector/amplifiers (each here referred to as a detector/preamp), the optical signal is converted into an associated electrical signal that has characteristics appropriate for further processing.

Channel A and B demodulators are associated with each of the detection (wavelength) channels. Channel A demodulators 2136, 2142, and 2148 are tuned to demodulate a signal characterized by a frequency or spectrum imbued to channel A illumination by RF Source A 2106a and Modulator A 2104a. Channel B demodulators 2138, 2144, and 2150 are tuned to demodulate a signal characterized by a frequency or spectrum imbued to channel B illumination by RF Source B 2106b and Modulator B 2104b. Thus, demodulated signals 2137, 2143, and 2149 correspond to the RGB video signal associated with Scanning Module A 1201a and demodulated signals 2139, 2145, and 2151 correspond to the RGB video signal associated with Scanning Module B.

One way to tune a detector to a pulse modulation frequency is to use lock-in amplifier, which amplifies a signal at one or more particular frequencies. Lock-in amplifiers may include circuitry to convert the detected modulated signal to base band or, alternatively, may pass a modulated signal to the controller. The controller converts the signal into an image and performs other necessary functions appropriate for the application.

In some embodiments, channel A represents a "left eye" perspective on the FOV and channel B a "right eye" perspective on the FOV. One such embodiment is when scanning modules 1201a and 1201b are arranged according to the tip layout of FIG. 20.

The apparatus of FIG. 21 may be rearranged, combined, split, substitutions made, etc. as appropriate for the application.

Scanned beam imagers approximating SVGA resolution may have data rates on the order of 20 MHz. One way to operate a synchronous detector with a scanned beam imager is to pulse the beam at a frequency that is high compared to the data rate. For instance, the beam may be modulated at a rate of 20 to 200 times the data rate, resulting in a pulse rate of 400 MHz to 4 GHz. Such high pulse rates can be a challenge for detectors, however, often resulting in significant photon shot noise as well as practical design difficulties. In some embodiments, the pulse rate may be run at a small multiple of data rate, for example at 1 to 10 times the data rate, resulting in a more manageable pulse rate of 20 to 200 MHz.

The device of FIG. 21 may operate at a pre-determined pulse frequency. It may desirable, particularly in low frequency multiple embodiments, to maintain a constant phase relationship between pixel clocking and synchronous pulse modulation in order to ensure an equal number of pulse modulation cycles. However, resonant scanning technologies do not have constant rotational velocities.

For resonant scanning systems, constant frequency pulse modulation may be used with constant pixel clock rate and variable pixel spacing. In this mode, it may be desirable to apply image processing to interpolate between actual sample locations to produce a constant pitch output. In this case, the addressability limit is set at the highest velocity point in the scan as the beam crosses the center of the FOV. More peripheral areas at each end of the scan where the scan beam is moving slower are over-sampled. In general, linear interpolation, applied two-dimensionally where appropriate, has been found to yield good image quality and have a relatively modest processing requirement. U.S. Provisional Patent Application No. 60/381,569 filed May 17, 2002 and entitled IMAGE QUALITY CONSIDERATIONS IN BI-SINUSOIDALLY SCANNED RETINAL SCANNING DISPLAY SYSTEMS, commonly assigned and hereby incorporated by reference teaches methods of interpolating pixel values, particularly with respect to bi-sinusoidal scanning.

Alternatively, constant pixel spacing may be maintained by varying both pixel clocking and synchronous pulse modulation frequency. Methods and apparatus for varying pixel clocking across a FOV are described in U.S. patent application Ser. No. 10/118,861 entitled ELECTRONICALLY SCANNED BEAM DISPLAY commonly assigned and hereby incorporated by reference.

FIG. 22 is an idealized diagram showing the waveforms for a pair of multiplexed beams. Linear fields of view 111a and 111b represent scan paths for scanning channels A and B, respectively. FOV 111a comprises a light region 502a and a gray region 506a aligned as indicated. FOV 111b comprises two light regions, 502b and 502b', surrounding a gray region 506b aligned as indicated. Note that FOVs 111a and 111b may be, and in this example are, distinct from one another at least in terms of feature alignment.

Waveform 2202a represents the modulation pattern of the channel A illuminator, aligned with the channel A FOV as shown. The high portions of the waveform represent an "on" condition of the illuminator while the low portions represent an off condition. Note that if combined with the illuminator power modulation of FIGS. 2 through 6, the illumination modulation waveforms could be more complex than shown in FIG. 22. However, the principles remain the same with respect to multiplexing and demultiplexing of channels.

Similarly, Waveform 2202b represents the modulation pattern of the channel B illuminator, aligned with the channel B FOV as shown. Note that channel A and B illuminators are modulated at different instantaneous frequencies to allow for differentiation and separation. As shown, both channels A and B are shown modulated at constant frequencies over the intervals shown. In some applications, it may be desirable to ensure that channels are modulated at non-integer multiples of one-another.

Waveform 2204 represents an idealized combined response received by a detector. Waveforms 2206a and 2206b represent the channel-specific components of waveform 2204—that is they may be determined from waveform 2204 and add to produce waveform 2204. Waveform 2206a represents the modulated response of channel A while waveform 2206b represents the modulated response of channel B. It may be noted that light areas 502 produce a response two units in height, gray areas 506 produce a response one unit in height, and the "off" cycle of waveforms 2202a and 2202b result in a null response.

Waveforms 2208a and 2208b represent demultiplexed, base band responses of channels A and B, respectively. It may be seen that light areas 502 create a high state while gray areas 506 create a low state. Note that to produce these base band waveforms, we have for convenience, adopted the convention of setting "off" portions of the modulation cycles equal to the response of the subsequent "on" portions. Waveforms 2208a and 2208b may, in turn, be interpreted or displayed as linear images 2209a and 2209b, respectively. A channel image 2209a has a light area 2210a and a dark area 2212a, while B channel image 2209b has two light areas 2210b and 2210b' surrounding a dark area 2212b. Thus it can be seen that the multiplexing/demultiplexing schema of FIG. 22 results in a plurality of images being simultaneously captured and properly decoded.

Figure 23:
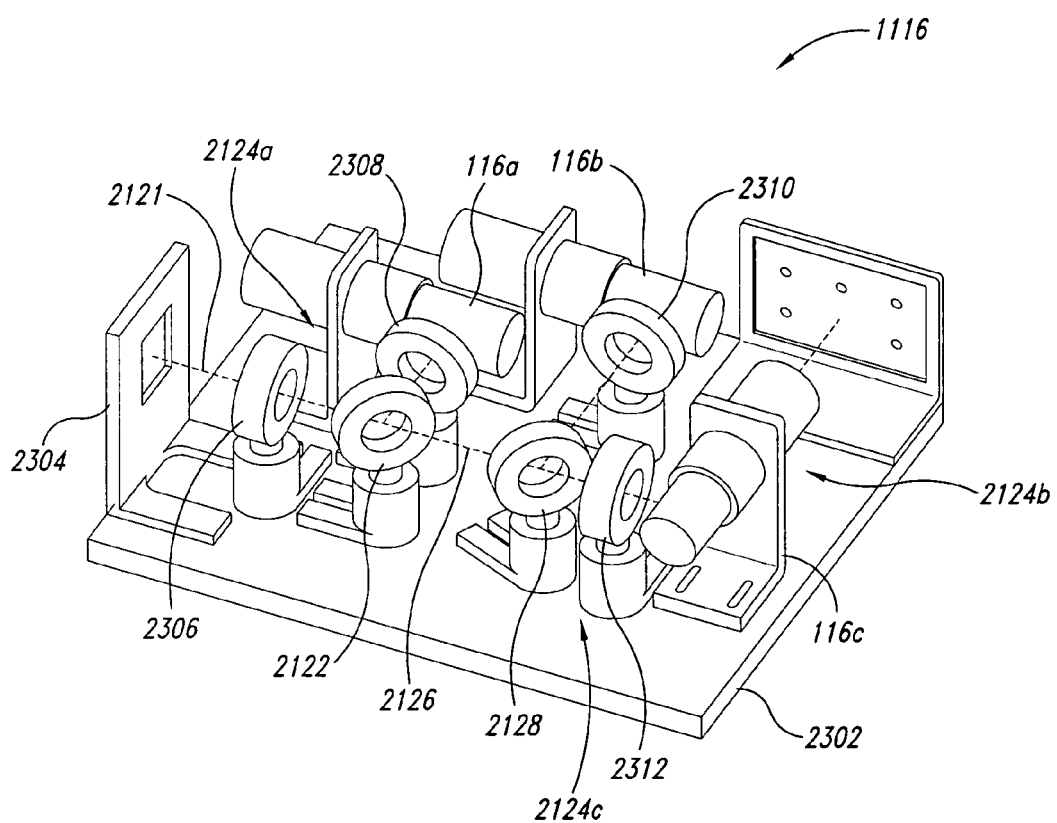
FIG. 23 is an isometric view of a detector module.

FIG. 23 is an isometric view of a detector module 1116. Within detector module 1116, the scattered light signal is separated into its wavelength components, for instance RGB. For some applications, for example those that use fluorescence or other color shifting imaging techniques, it may be desirable to detect additional or alternative wavelengths from those emitted by the illuminator.

Optical base 2302 is a mechanical component to which optical components are mounted and kept in alignment. Additionally, base 2302 provides mechanical robustness and, optionally, heat sinking. The incoming detection fiber or fibers are terminated at fiber mount 2304 and further light transmission is made via the free space optics depicted in FIG. 23. Focusing lens 2306 shapes the light beam, which 2306 that emerges from the fiber mount. Mirror 2122, which may be a dielectric mirror, splits off a blue light beam 2124a and directs it to the blue detector assembly. The remaining composite signal 2126, comprising green and red light, is split by dielectric mirror 2128. Dielectric mirror 2128 directs green light 2124b toward the green detector assembly, leaving red light 2124c to pass through to the red detector assembly.

Blue green and red detector assemblies comprise blue, green, or red filters 2308, 2310, or 2312, respectively, and a photomultiplier tube (PMT) 116. The filters serve to further isolate the detector from any crosstalk, which may be present in the form of light of unwanted wavelengths. For one embodiment, HAMMAMATSU model R1527 PMT was found to give satisfactory results. This tube had an internal gain of approximately 10,000,000, a response time of 2.2 nanoseconds, a side-viewing active area of 8×24 millimeters, and a quantum efficiency of 0.1. Other commercially available PMTs may be satisfactory as well.

For the PMT embodiment of the device, two stages of amplification, each providing approximately 15 dB of gain for 30 dB total gain, boosted the signals to levels appropriate for analog-to-digital conversion. The amount of gain varied slightly by channel (ranging from 30.6 dB of gain for the red channel to 31.2 dB of gain for the blue channel), but this was not felt to be particularly critical because subsequent processing would maintain white balance.

In another embodiment, avalanche photodiodes (APDs) were used in place of PMTs. The APDs used included a thermo-electric (TE) cooler, TE cooler controller, and a transimpedence amplifier. The output signal was fed through another 5× gain using a standard low noise amplifier.

In addition to PMTs and APDs, other light detectors may be used.

Figure 24:
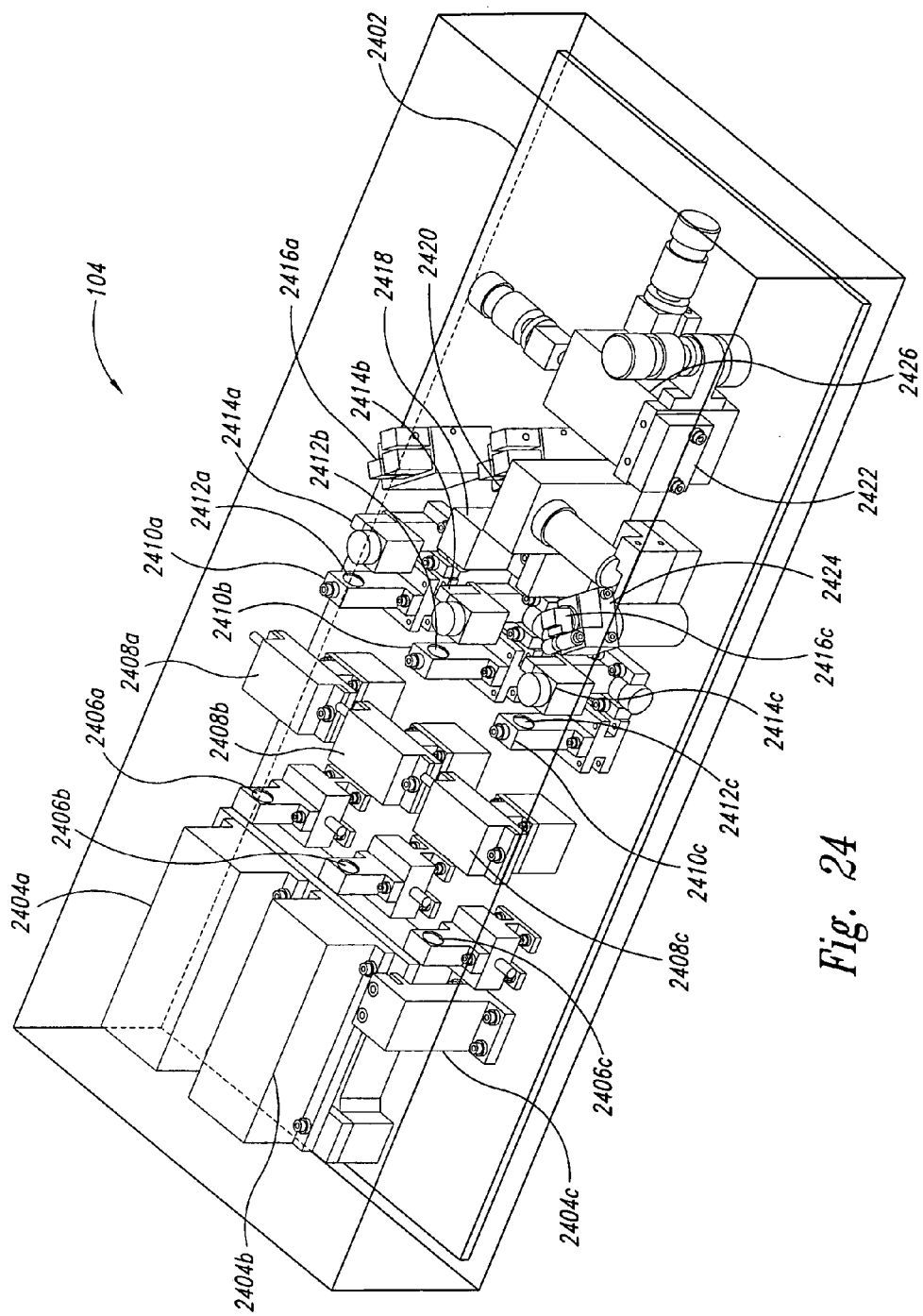
FIG. 24 is an isometric view of a light source module.

FIG. 24 is an isometric view of a light source module or illuminator 104 having three laser emitters providing RGB illumination. Blue, green, and red lasers 2404a, 2404b, and 2404c, respectively, illuminate through substantially identical optical components until they are combined. In one embodiment, the blue laser 2404a was a B&W TEK 10 mW diode-pumped solid state (DPSS) laser emitting at 473 nanometers (nm); the green laser 2404b was a B&W TEK 15 mW DPSS laser emitting at 532 nm, and the red laser 2404c was a HITACHI 35 mW circularized laser diode emitting at 635 nm. For applications where white balancing done in software, it is not necessary to equalize the output power (or apparent output power in the presence of detector non-uniformity) between the channels.

Beams from blue, green, and red lasers 2404a, 2404b, and 2404c pass through focusing lenses 2406a, 2406b, and 2406b prior to passing through acousto-optic modulators (AOMs) 2408a, 2408b, and 2408c, respectively. The focusing lenses are set to focus the beams at the center of the AOM crystals. After passing through AOMs 2408a, 2408b, and 2408c, the blue, green, and red beams pass through beam blocks 2410a, 2410b, and 2410c and then through collimating lenses 2412a, 2412b, and 2412c, respectively. The beam blocks are vertical slits that block all but the 1$^{st}$ order diffractive harmonic emerging from the AOMs. Parallel plate optic (PPO) devices 2414a, 2414b, and 2414c are used to align the beams with respect to vertical and lateral displacement. Dielectric mirrors 2416a and 2416c turn the blue and red beams, respectively toward beam combiner 2418, into which the green beam is directly introduced. In one embodiment, beam combiner 2418 was an X-cube. Dielectric mirror 2420 redirects the combined beam, which now appears whitish, toward microscope objective 2422, which focuses the beam onto the core of the illumination fiber held in CF optical fiber mount 2424. Three-axis micrometer 2426 is used to align the fiber core to the beam. In one embodiment, microscope objective 2422 was a chromatic dispersion controlled 20× objective. The illumination fiber (not shown) was an angled tip single mode glass fiber with a 3.5 micron core and 125 micron cladding.

While the illuminator module 104 of FIG. 24 was constructed of off-the-shelf components, equivalent designs using custom or off-the-shelf components may be appropriate. In some embodiments, it may be desirable to build an entirely fiber-coupled system. In this and other cases, beam combining may be effectively done using evanescent coupling, for instance.

Figure 25:
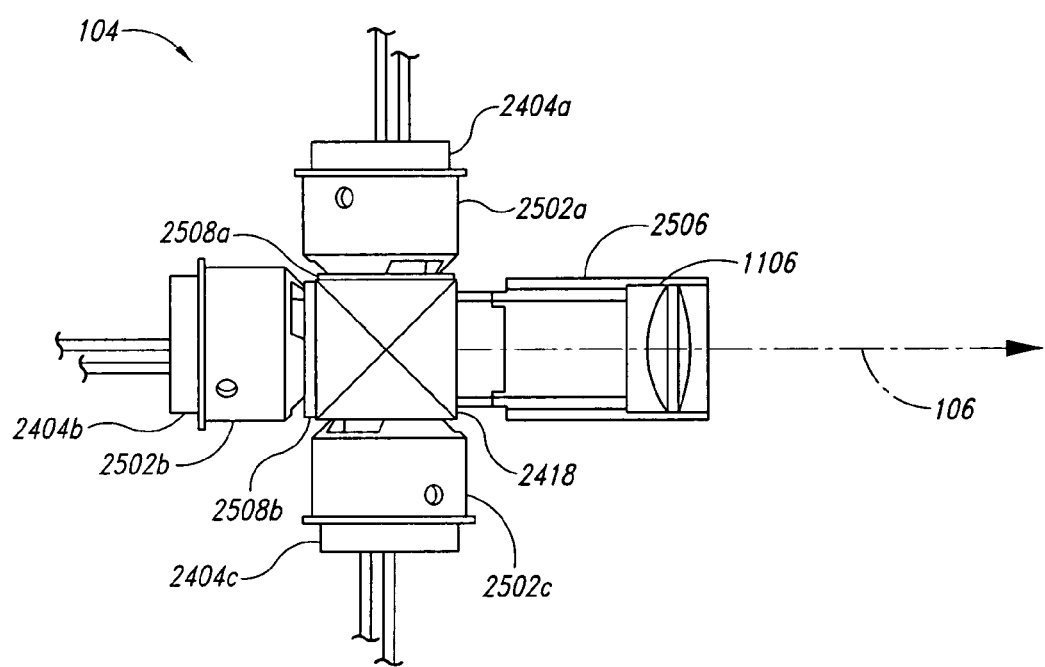
FIG. 25 is a side view of a compact three color light source where the output beams are combined by an X-cube.

One example of an alternative, directly modulated illuminator 104 is shown in FIG. 25. FIG. 25 is a compact illuminator or light source module 104 having three emitters. The emitters of FIG. 25, which may be laser diodes or light emitting diodes, may be directly modulated as required. This may be particularly advantageous, for example, when used with an embodiment that puts the illuminators and detectors in the hand piece 1012. Emitters 2404a, 2404b, and 2404c, which may for instance be RGB lasers or edge-emitting LEDs, are held by mounts 2502a, 2502b, and 2502c, respectively. Mounts 2502 may include provision for aligning the emitters. Light beams output by emitters 2404a, 2404b, and 2404c are combined by X-cube 2504 and output along a common axis as combined beam 106. X-cube 2504 may be a commercially available birefringent device. The output beam 106 proceeds down mounting barrel 2506 and is collimated or focused by output optic 1106, here shown as a doublet. Alternatively, output optic 1106 may be include a single lens and/or an aperture (not shown). Spacers 2508a and 2508b vary the optical path length between the three illuminators 2404a, 2404b, and 2404c and output optic 1106, thus compensating for chromatic aberration.

Figure 26A:
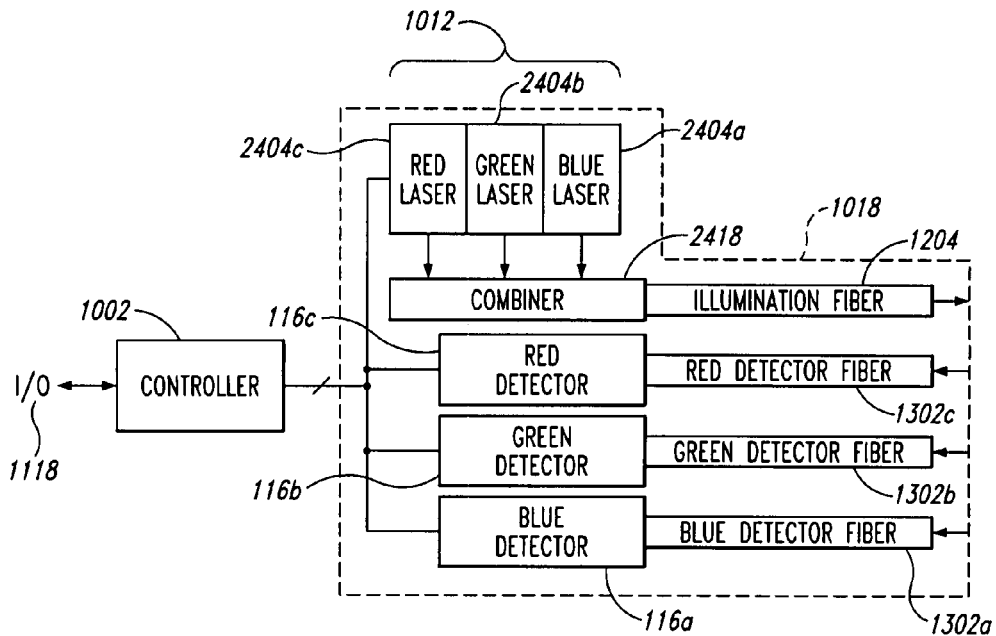
FIG. 26a is a block diagram of the proximal end of an endoscope.
Figure 26B:
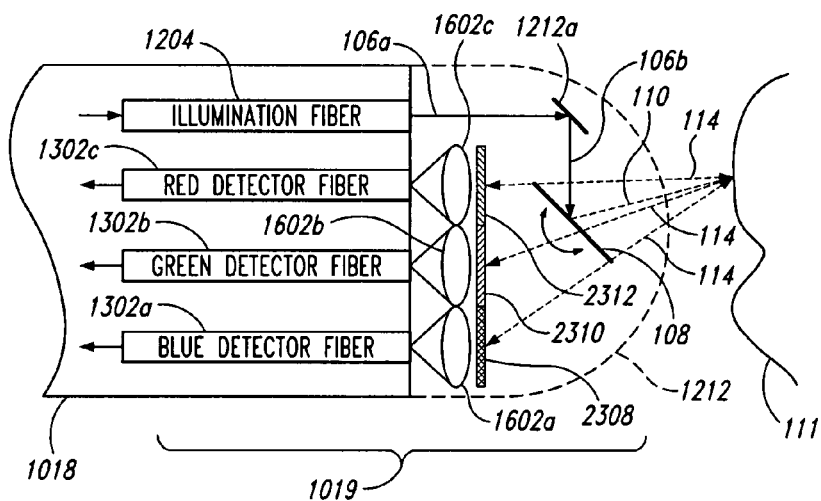
FIG. 26b is a block diagram of the distal end of an endoscope.

FIGS. 26a and 26b comprise a block diagram of an alternative embodiment of a scanning endoscope or laparoscope. A proximal body 1012, which may comprise a hand piece and/or a separate console, is attached to a tip 1018. The coupling between proximal body 1012 and tip 1018 may be removable, thus allowing interchangeability of tips, and optionally disposability of tips. A controller 1002, which may be combined with or separate from proximal body 1012, is operatively coupled to one or more illuminators and detectors in proximal body 1012. Interface 1118 provides for communication with external data sources and sinks such as displays, actuators, remote experts, etc.

In some embodiments, the illuminator may comprise separate blue, green, and red lasers 2404a, 2404b, and 2404c, respectively. Output from the laser emitters is combined into a single light signal in a beam combiner 2418. Beam combiner 2418 may then be coupled to illuminator fiber 1204, and the illumination energy sent down the tip.

At the distal end 1019 of tip 1018, light emerges from illumination fiber 1204 to be scanned across the field-of-view 111. In the particular embodiment diagrammatically shown here, output beam 106a is redirected by a turning mirror 1212a, which may be a metal or a dielectric mirror for example, toward scanning mirror 108. The scanned beam 110 is emitted through protective transparent cover 1212 toward the field-of-view 111.

A portion of the reflected or scattered light 114 passes back through transparent protective cover 1212 to be gathered by return fibers 1302. In the particular embodiment illustrated, separate detector fibers 1302a, 1302b, and 1302c are used to gather and return blue, green, and red signals, respectively. Light signals may be separated by placing filters 2308, 2310, and 2312 over the blue, green and red fibers 1302a, 1302b, and 1302c, respectively. Optional light coupling elements 1602a, 1602b, and 1602c may be used to increase the light gathering efficiency of the detector fibers, thus boosting the optical signal strength or making it more uniform across the field-of-view.

Blue, green, and red detector fibers 1302a, 1302b, and 1302c transmit received optical energy up the tip and transmit it to blue, green, and red detectors 116a, 116b, and 116c, respectively, in the proximal body 1012. Detectors 116 convert the received light energy into electrical signals for processing and decoding into an image by controller 1002.

As an alternative to tip-mounted filters, the filters may be coupled more directly with the detectors with all the detector fibers carrying all wavelengths of received light energy. This arrangement, while it may result in larger required gathering optic size or reduced signal strength, may help to isolate detector channels and reduce optical crosstalk.

Figure 27:
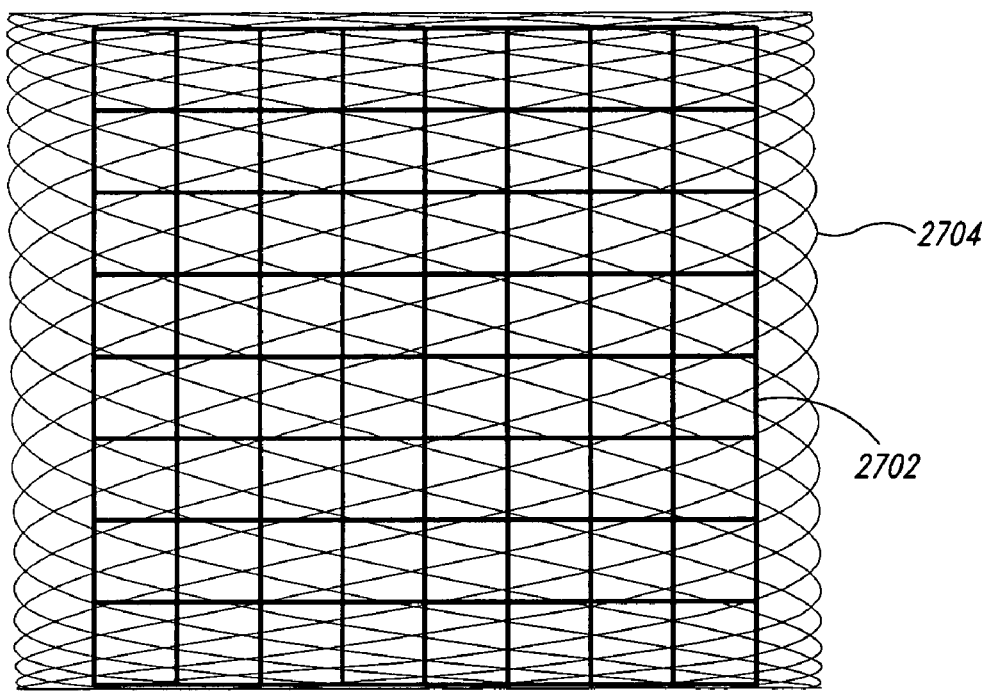
FIG. 27 is an idealized image showing a bisinusoidal scan pattern.

High speed MEMS mirrors and other resonant deflectors may be characterized by sinusoidal scan rates, compared to constant rotational velocity scanners such as rotating polygons. To reduce power requirements and size constraints at the imaging tip, some embodiments may allow both scan axes to scan resonantly. A resultant idealized bi-resonant or bi-sinusoidal scan pattern is shown in FIG. 27. In certain instances, the scan pattern follows at path characterized as a Lissajous pattern. Rectilinear matrix 2702 is shown overlaid with bi-resonant scan path 2704. In this case, the intersections between the vertical and horizontal lines of the rectilinear matrix represent idealized pixel positions while bi-resonant scan path 2704 represents the actual path taken by the scanned spot. As may be seen, the actual scan path doesn't align perfectly with all the rectilinear pixel positions. These values may therefore be determined by interpolating.

Methods for selecting bi-resonant frequencies as well as methods for maximizing the image quality are discussed analogously in the U.S. Patent Application entitled IMAGE QUALITY CONSIDERATIONS IN BI-SINUSOIDALLY SCANNED RETINAL SCANNING DISPLAY SYSTEMS, by Margaret Brown, Marc Freeman, and John R. Lewis, application Ser. No. 10/441,916, applied for May 19, 2003, commonly assigned herewith and hereby incorporated by reference. That patent application, among other things, teaches methods of interpolating pixel values, particularly with respect to bi-sinusoidal scanning.

For resonant scanning systems, constant frequency pulse modulation may be used with constant pixel clock rate and variable pixel spacing. In such a mode, it may be desirable to apply image processing to interpolate between actual sample locations to produce a constant pitch output. In this case, the addressability limit is set at the highest velocity point in the scan as the beam crosses the center of the FOV. More peripheral areas at each end of the scan where the scan beam is moving slower are over-sampled. In general, linear interpolation applied two-dimensionally has been found to yield good image quality and have a relatively modest processing requirement.

Alternatively, constant pixel spacing may be maintained by varying both pixel clocking and synchronous pulse modulation frequency. Methods and apparatus for varying pixel clocking across a FOV are described in U.S. patent application Ser. No. 10/118,861 entitled ELECTRONICALLY SCANNED BEAM DISPLAY by Gregory Scott Bright; Scott W. Straka; Philip C. Black; James G. Moore; John R. Lewis; Hakan Urey; Clarence T. Tegreene, filed Apr. 9, 2002, commonly assigned herewith and hereby incorporated by reference.

By using a clock divider (for frequency ratios greater than 1:1) or a second clock, one may use the apparatus disclosed therein to also control pulse modulation frequency synchronously with pixel clocking. This may be used in conjunction with the apparatus of FIG. 21 to produce the separable light modulation used by illuminators A and B 104a and 104b, respectively.

The preceding overview of the invention, brief description of the drawings, and detailed description describe exemplary embodiments of the present invention in a manner intended to foster ease of understanding by the reader. Other structures, methods, and equivalents may be within the scope of the invention. As such, the scope of the invention described herein shall be limited only by the claims.

What is claimed is:

1. A method for capturing an image, comprising:
creating a beam of light;
scanning the beam of light across a two-dimensional field-of-view at a rate non-constant in both axes;
collecting scattered light with one or more optical fibers; and
detecting light from the field-of-view;
sampling data at a substantially constant rate; and,
interpolating between the sampled data points to produce an image having substantially equal spacing between pixels.

2. The method for capturing an image of claim 1, wherein said step of scanning the beam of light, further comprises:
scanning along a first scan axis scanned at a first scan frequency; and
scanning along a second scan axis scanned at a second scan frequency;
wherein the second scan frequency is lower than the first scan frequency; and
wherein at least one of said axes is scanned at a sinusoidally varying scan speed.

3. A method for capturing an image, comprising:
creating a beam of light;
scanning the beam of light across a two-dimensional field-of-view at a rate non-constant in both axes, including scanning along a first scan axis scanned at a first scan frequency and scanning along a second scan axis scanned at a second scan frequency, wherein the second scan frequency is lower than the first scan frequency, and wherein at least one of said axes is scanned at a sinusoidally varying scan speed;
collecting scattered light with one or more optical fibers; and
detecting light from the field-of-view;
wherein data is sampled at an instantaneous rate substantially inversely proportional to the instantaneous scan speed along the axis that is scanned at a sinusoidally varying scan speed.

4. The method for capturing an image of claim 3, wherein the two-dimensional field-of-view is sampled at a frame rate and both of said first and second scan axes are scanned at frequencies higher than the frame rate.

5. The method of claim 4, wherein the beam is scanned in a Lissajous scan pattern.

* * * * *